US011992325B2

(12) United States Patent
Ejaz et al.

(10) Patent No.: US 11,992,325 B2
(45) Date of Patent: May 28, 2024

(54) SYSTEMS, DEVICES AND METHODS FOR DEXTROUS HAND FUNCTION ASSESSMENT AND THERAPY

(71) Applicant: MINDMAZE GROUP SA, Lausanne (CH)

(72) Inventors: Naveed Ejaz, Lausanne (CH); Nicolas Fremaux, Lausanne (CH); Sylvain Cardin, Lausanne (CH); Mouna Cerra Cheraka, Lausanne (CH); Gangadhar Garipelli, Lausanne (CH)

(73) Assignee: MINDMAZE GROUP SA, Lausanne (CH)

( * ) Notice: Subject to any disclaimer, the term of this patent is extended or adjusted under 35 U.S.C. 154(b) by 126 days.

(21) Appl. No.: 17/102,457

(22) Filed: Nov. 24, 2020

(65) Prior Publication Data

US 2022/0160290 A1 May 26, 2022

Related U.S. Application Data

(60) Provisional application No. 62/939,108, filed on Nov. 22, 2019, provisional application No. 62/939,115, filed on Nov. 22, 2019.

(51) Int. Cl.
*A61B 5/00* (2006.01)
*A61B 5/11* (2006.01)

(52) U.S. Cl.
CPC .......... *A61B 5/4076* (2013.01); *A61B 5/0002* (2013.01); *A61B 5/11* (2013.01);
(Continued)

(58) Field of Classification Search
CPC .................. A61B 5/1125; A61B 5/225; A61B 2560/0214; A61B 5/02438; A61B 5/6898;
(Continued)

(56) References Cited

U.S. PATENT DOCUMENTS

| 3,898,983 A | * | 8/1975 | Elam | ...................... A61B 5/103 600/595 |
| 2007/0129767 A1 | * | 6/2007 | Wahlstrand | ........... H02J 50/402 607/33 |

(Continued)

OTHER PUBLICATIONS

A hand rehabilitation exercise system for people with stroke (HandREPS) A Thesis submitted by Akhil Mohan for the award of the degree of Doctor of Philosophy Department of Biotechnology, Bhupat and Jyoti Mehta School of Biosciences Indian Institute of Technology Madras Aug. 2018, 150 pages.

(Continued)

*Primary Examiner* — Yi-Shan Yang
*Assistant Examiner* — Jonathan E. Cooper
(74) *Attorney, Agent, or Firm* — GRAESER ASSOCIATES INTERNATIONAL INC; Dvorah Graeser

(57) ABSTRACT

Devices, methods and systems related to the assessment and therapy of neurological conditions and dexterous hand function in particular. For example, some embodiments can relate to devices comprising a first portion of flexible material and forming a cavity; a second portion non-flexible material; a PCB coupled to the second portion; and wherein a portion of an edge of the first portion is configured to create a semi-hermetic seal with at least a portion of an edge of the second portion and the PCB has connected thereto a pressure sensor, a wireless transceiver, and a power storage unit.

23 Claims, 27 Drawing Sheets

(52) U.S. Cl.
CPC .......... *A61B 5/4836* (2013.01); *A61B 5/6825* (2013.01); *A61B 5/742* (2013.01); *A61B 2562/0219* (2013.01); *A61B 2562/0247* (2013.01)

(58) Field of Classification Search
CPC .......... A61B 5/6824; A61B 2560/0209; A61B 5/1114; A61B 5/6801; A61B 5/022; A61B 2018/1226; A61B 17/7016; A61B 5/6825; A61B 2017/00734; A61B 5/6828; A61B 5/6806; A61B 5/6829; A61B 5/6826; A61B 1/00034; A61B 5/6822; A61B 5/150129; A61B 2560/0425; A61B 2560/0223; A61B 5/4076; A61B 5/0002; A61B 5/11; A61B 5/4836; A61B 5/742; A61B 2562/0219; A61B 2562/0247; A61M 60/873; A61M 2205/3358; H02J 50/00; H01F 38/14
See application file for complete search history.

(56) References Cited

U.S. PATENT DOCUMENTS

| | | | |
|---|---|---|---|
| 2016/0067136 A1* | 3/2016 | Raghavan | A61B 5/225 601/40 |
| 2017/0265802 A1* | 9/2017 | Bromm | A61B 5/4824 |
| 2017/0307452 A1* | 10/2017 | Lafian | G01N 7/10 |
| 2019/0159714 A1* | 5/2019 | Nagasu | A63B 24/0062 |
| 2021/0204880 A1* | 7/2021 | Cedrone | A61B 5/02438 |
| 2022/0079437 A1* | 3/2022 | Suzuki | A61B 3/16 |

OTHER PUBLICATIONS

A. Mohan et al., "An instrumented object for hand exercise and assessment using a pneumatic pressure sensor" Review of Scientific Instruments 89, 055004-1-9 (2018) 10 pages.
Balasubramanian S, Klein J, Burdet E. Robot-assisted rehabilitation of hand function. Curr Opin Neurol. Dec. 2010;23(6):661-70.
E. Burdet et al., "Stability and motor adaptation in human arm movements" Biol Cybern (2006) 94: 20-32.
Ludovic Dovat et al., "HandCARE: A Cable-Actuated Rehabilitation System to Train Hand Function After Stroke" Transactions on Neural Systems and Rehabilitation Engineering 16 (6), 582-591, 2008.
O. Lambercy, L. Dovat, R. Gassert, E. Burdet, C. L. Teo and T. Milner, "A Haptic Knob for Rehabilitation of Hand Function," in IEEE Transactions on Neural Systems and Rehabilitation Engineering, vol. 15, No. 3, pp. 356-366, Sep. 2007, doi: 10.1109/TNSRE.2007.903913.
Rana Jaber et al., "Design and validation of the Grip-ball for measurement of hand grip strength" Medical Engineering & Physics (2012) 34. 1356-61.
S. Balasubramanian, A. Melendez-Calderon and E. Burdet, "A Robust and Sensitive Metric for Quantifying Movement Smoothness," in IEEE Transactions on Biomedical Engineering, vol. 59, No. 8, pp. 2126-2136, Aug. 2012, doi: 10.1109/TBME.2011.2179545.

\* cited by examiner

| Task-based Activities | Functional Activities |
|---|---|
| Izar (Frogger) | Izar (Amoeba) |
| Reach 2D | Magic Carpet |
| Butterflies | Space Burger |
| Lanterns | Reach 3D |
| Balloons | Izar (Flying Cat) |
| Botanica | Airplane |
| Tower Builder | Cross The Road |
| : | Magic 4 |
| : | Japanese Garden |
| : | Phoenix Bird |
| : | Bilateral |
| : | Ski-Liner |
| : | : |
| : | : |
| : | : |

Figure 18

| Order | Activity | No. of Reps | [Estimated] Duration [mins] | Total Duration [%] |
|---|---|---|---|---|
| 1. | Cross The Road | - | 10 | 8 % |
| 2. | Tower Builder | - | 10 | 8 % |
| 3. | Airplane | - | 10 | 8 % |
| 4. | Rest Break | | 5 | 4 % |
| 5. | Izar (Amoeba) | - | 20 | 16 % |
| 6. | Izar (Frogger) | 30 | 10 | 8 % |
| 7. | Reach 3D | 20 | 10 | 8 % |
| 8. | Rest Break | | 5 | 4 % |
| 9. | Izar (Flying Cat) | - | 15 | 12 % |
| 10. | Magic Carpet | - | 10 | 8 % |
| 11. | Rest Break | | 10 | 8 % |
| 12. | Izar (Amoeba) | - | 5 | 4 % |
| total scheduled duration | | | 120 mins | |

Figure 19

| Order | Activity | Value |
|---|---|---|
| 1. | Cross The Road | 1 |
| | level | |
| | difficulty settings: | |
| | - perceptual | medium |
| | - motor | hard |
| | - cognitive | easy |
| 2. | Tower Builder | 2 |
| | level | |
| | difficulty settings: | |
| | - perceptual | medium |
| | - motor | medium |
| | - cognitive | hard |
| | ... | ... |

Figure 20

SYSTEMS, DEVICES AND METHODS FOR DEXTROUS HAND FUNCTION ASSESSMENT AND THERAPY

FIELD OF THE DISCLOSURE

The present disclosure relates to devices, systems, and methods for the assessment and therapy of neurological conditions and conditions affecting dexterous hand function in particular.

BACKGROUND

For clinical practice, professional associations provide recommendations about which scales to use like the Academy of Neurological Physical Therapy (ANPT) in the United States. These recommendations are usually country and condition specific. It is up to each site to implement them in current practice.

For clinical research, the Stroke Recovery and Rehabilitation Roundtable (SRRR) have published this year guidelines about how to measure quality of movement for upper limb in patients suffering from stroke (Kwakkel et al. 2019).

In current practice, each clinic is using its own set of scales in order to assess patients' impairments.

Typically, impairments are assessed in isolation, it is rare to have a full battery of assessments that include upper limbs, lower limbs, hand and cognition. Performing the assessment is time consuming and gives you a score with different degrees of sensitivity and variability. An automated multi-modal assessment would give the best fidelity in tracking impairments and providing a holistic view of patients' impairments.

Furthermore, a major challenge in neurorehabilitation is that recovery can either be behavioral restitution or behavioral compensation. It is critical to measure to deliver the most adequate therapy to each patient. The automated multimodal assessment could potentially overcome this challenge while removing inter-rater variability and saving time by integrating all dimensions in a gamified activity that is part of the patients' therapy treatment plan.

Physical and occupational therapists create tailored therapy plan for each patient based on the patient's medical record and their examination of the patient's nature of impairment and the associated severity. The therapy plan includes the type of therapy, the dosage as well as the schedule (i.e. how often the therapy sessions will take place). Finding the appropriate therapy plan is complicated without a holistic view of the patient's sensorimotor and cognitive impairments. Each therapist develops his/her own protocols to treat patients depending on if he is a physical therapist, an occupational therapist or a neuropsychologist. This lack of homogeneity prevents the field from identifying the optimal therapy treatment according to the patient's level of impairment.

Moreover, these problems are magnified in cases where treatment options are limited or fail to target specific areas in need of either assessment or therapy. One such area is hand function. Humans have a unique ability to use their hands in a dexterous manner to manipulate and interact with the environment around them. Dexterous hand function in humans is primarily controlled by the corticospinal pathway. The corticospinal pathway can be damaged because of neurological insult (e.g., stroke, spinal cord injury). Since the corticospinal pathway is the primary pathway that controls hand function, dexterous hand function is impaired in patients suffering from a neurological insult.

In neurorehabilitation, the current focus in hand training is mostly corrupted by strength requirements of the task. Consequently, most clinical instruments and devices primarily measure deficits in strength. There is currently no valuable clinical instrument nor device to measure deficits in dexterity. After brain injury, there are some stereotypical deficits that emerge:

Loss of hand control masked by synergies.

Inability to fully open the hand due to problems focally engaging extensor muscles.

Impaired ability to perform functional tasks (e.g., grabbing and stabilizing a cup).

Current devices and methods fail to take into account these deficits without measuring and treating strength either as a primary function or because of inherent bias. For example, dynamometers and other devices and their methods that measure force exhibit this bias towards training strength.

In neurorehabilitation, even clinical instruments and methods that are intended to measure dexterity fail to isolate dexterity properly. Such methods include the Box and Block Test and the Nine Whole Peg Test. Such devices and methods additionally cannot be used with patients that have severe dexterity deficits. That is, a minimum dexterity is needed to be able to execute the tasks included in these instruments. It is uncertain if improvement in dexterity as measured with these instruments is really reflecting improvement in dexterity rather than functional improvement related to the learning phase of the tasks included in these instruments.

Other existing technologies meant to train dexterity deficits (e.g., Gloreha Sinfonia, MusicGlove, HandTutor and Neofect) use intensity and dosage as measures for dexterity, which is not sufficient as a measure.

Thus, what is needed is a device and methods for integrating a logic targeting the training of these impairments/functions and that are sensitive enough to measure dexterity deficits objectively.

SUMMARY OF SOME OF THE EMBODIMENTS

Therapists can use various embodiments of the devices and methods described herein for whole hand grasp training, pincer grasp training, as well as in other configurations. Such devices and methods can be used in different postures allowing spastic patients to train with them.

Some embodiments of the present disclosure are peripheral devices that can connect via Bluetooth and allow game interactions by providing information about grasp force and orientation. Some embodiments are egg-shaped devices that the user holds in the hand and a base station for charging and pressure resetting.

Advantages of embodiment of the present disclosure including allowing the objective measurement of dexterity deficits and training dexterity deficit using the same hand device.

Optionally, some embodiments of the present disclosure can relate to a device for providing dexterous hand function assessment and therapy, comprising a first portion of flexible material and forming a cavity; a second portion non-flexible material; a printed circuit board (PCB) coupled to the second portion; and wherein a portion of an edge of the first portion is configured to create a semi-hermetic seal with at least a portion of an edge of the second portion and the PCB has connected thereto a pressure sensor, a wireless transceiver, and a power storage unit.

Optionally, some embodiments of the present disclosure can relate to a device for providing dexterous hand function assessment and therapy, comprising a first portion of flexible material and forming a cavity; a second portion non-flexible material; a PCB coupled to the second portion; wherein a portion of an edge of the first portion is configured to create a semi-hermetic seal with at least a portion of an edge of the second portion and the PCB has connected thereto a pressure sensor, a wireless transceiver, and a power storage unit; and further comprising a valve through the second portion and wherein the second portion includes a substantially flat facet.

Optionally, some embodiments of the present disclosure can relate to a device for providing dexterous hand function assessment and therapy, comprising a first portion of flexible material and forming a cavity; a second portion non-flexible material; a PCB coupled to the second portion; wherein a portion of an edge of the first portion is configured to create a semi-hermetic seal with at least a portion of an edge of the second portion and the PCB has connected thereto a pressure sensor, a wireless transceiver, and a power storage unit; and further comprising a valve through the second portion and wherein the second portion includes a substantially flat facet; and further comprising one or more inertial measurement units (IMU) and a memory storage device.

Optionally, some embodiments of the present disclosure can relate to a device for providing dexterous hand function assessment and therapy, comprising a first portion of flexible material and forming a cavity; a second portion non-flexible material; a PCB coupled to the second portion; wherein a portion of an edge of the first portion is configured to create a semi-hermetic seal with at least a portion of an edge of the second portion and the PCB has connected thereto a pressure sensor, a wireless transceiver, and a power storage unit; and further comprising a valve through the second portion and wherein the second portion includes a substantially flat facet; further comprising one or more inertial measurement units (IMU) and a memory storage device; and wherein the first portion comprises a graphical component to enable position and orientation tracking of the device.

Optionally, some embodiments of the present disclosure can relate to a device for providing dexterous hand function assessment and therapy, comprising a first portion of flexible material and forming a cavity; a second portion non-flexible material; a PCB coupled to the second portion; wherein a portion of an edge of the first portion is configured to create a semi-hermetic seal with at least a portion of an edge of the second portion and the PCB has connected thereto a pressure sensor, a wireless transceiver, and a power storage unit; and further comprising a valve through the second portion and wherein the second portion includes a substantially flat facet; and further comprising one or more inertial measurement units (IMU) and a memory storage device; and an active marker to enable position and orientation tracking of the device.

Optionally, some embodiments of the present disclosure can relate to a device for providing dexterous hand function assessment and therapy, comprising a first portion of flexible material and forming a cavity; a second portion non-flexible material; a PCB coupled to the second portion; wherein a portion of an edge of the first portion is configured to create a semi-hermetic seal with at least a portion of an edge of the second portion and the PCB has connected thereto a pressure sensor, a wireless transceiver, and a power storage unit; and further comprising a valve through the second portion and wherein the second portion includes a substantially flat facet; and further comprising one or more inertial measurement units (IMU) and a memory storage device; an active marker to enable position and orientation tracking of the device; and a third portion through which the active marker is visible.

Optionally, some embodiments of the present disclosure can relate to a system for providing dexterous hand function assessment and therapy, comprising a device for providing dexterous hand function assessment and therapy, comprising a first portion of flexible material and forming a cavity; a second portion non-flexible material; a PCB coupled to the second portion; and wherein a portion of an edge of the first portion is configured to create a semi-hermetic seal with at least a portion of an edge of the second portion and the PCB has connected thereto a pressure sensor, a wireless transceiver, and a power storage unit; and further comprising a base station comprising a battery charging component, the battery charging component including a cooling system.

Optionally, some embodiments of the present disclosure can relate to a method for the assessment and therapy of dexterous hand function, comprising establishing a connection with a hand device; establishing a hand selection assigned to the hand device; receiving a first barometric pressure of the interior of the hand device; sending an instruction to an idle pressure controller indicating the barometric pressure is a baseline.

Unless otherwise defined, all technical and scientific terms used herein have the same meaning as commonly understood by one of ordinary skill in the art to which this disclosure belongs. The materials, methods, and examples provided herein are illustrative only and not intended to be limiting.

Various embodiments of the methods, systems and apparatuses of the present disclosure can be implemented by hardware and/or by software or a combination thereof. For example, as hardware, selected steps of methodology according to some embodiments can be implemented as a chip and/or a circuit. As software, selected steps of the methodology (e.g., according to some embodiments of the disclosure) can be implemented as a plurality of software instructions being executed by a computer (e.g., using any suitable operating system). Accordingly, in some embodiments, selected steps of methods, systems and/or apparatuses of the present disclosure can be performed by a processor (e.g., executing an application and/or a plurality of instructions).

Although embodiments of the present disclosure are described with regard to a "computer," and/or with respect to a "computer network," it should be noted that optionally any device featuring a processor and the ability to execute one or more instructions is within the scope of the disclosure, such as may be referred to herein as simply a computer or a computational device and which includes (but not limited to) any type of personal computer (PC), a server, a cellular telephone, an IP telephone, a smartphone or other type of mobile computational device, a PDA (personal digital assistant), a thin client, a smartwatch, head mounted display or other wearable that is able to communicate wired or wirelessly with a local or remote device. To this end, any two or more of such devices in communication with each other may comprise a "computer network."

BRIEF DESCRIPTION OF THE DRAWINGS

Embodiments of the disclosure are herein described, by way of example only, with reference to the accompanying drawings. With specific reference now to the drawings in detail, it is stressed that particulars shown are by way of example and for purposes of illustrative discussion of the various embodiments of the present disclosure only and are presented in order to provide what is believed to be a useful and readily understood description of the principles and conceptual aspects of the various embodiments of inventions disclosed therein.

FIG. 18 illustrates a catalog of activities in an exemplary system of assessment and therapy in accordance with embodiments.

FIG. 19 illustrates a therapy plan structure in an exemplary system of assessment and therapy in accordance with embodiments.

FIG. 20 illustrates a detailed view of a therapy plan structure in an exemplary system of assessment and therapy in accordance with embodiments.

DETAILED DESCRIPTION OF SOME OF THE EMBODIMENTS

Figure 1:
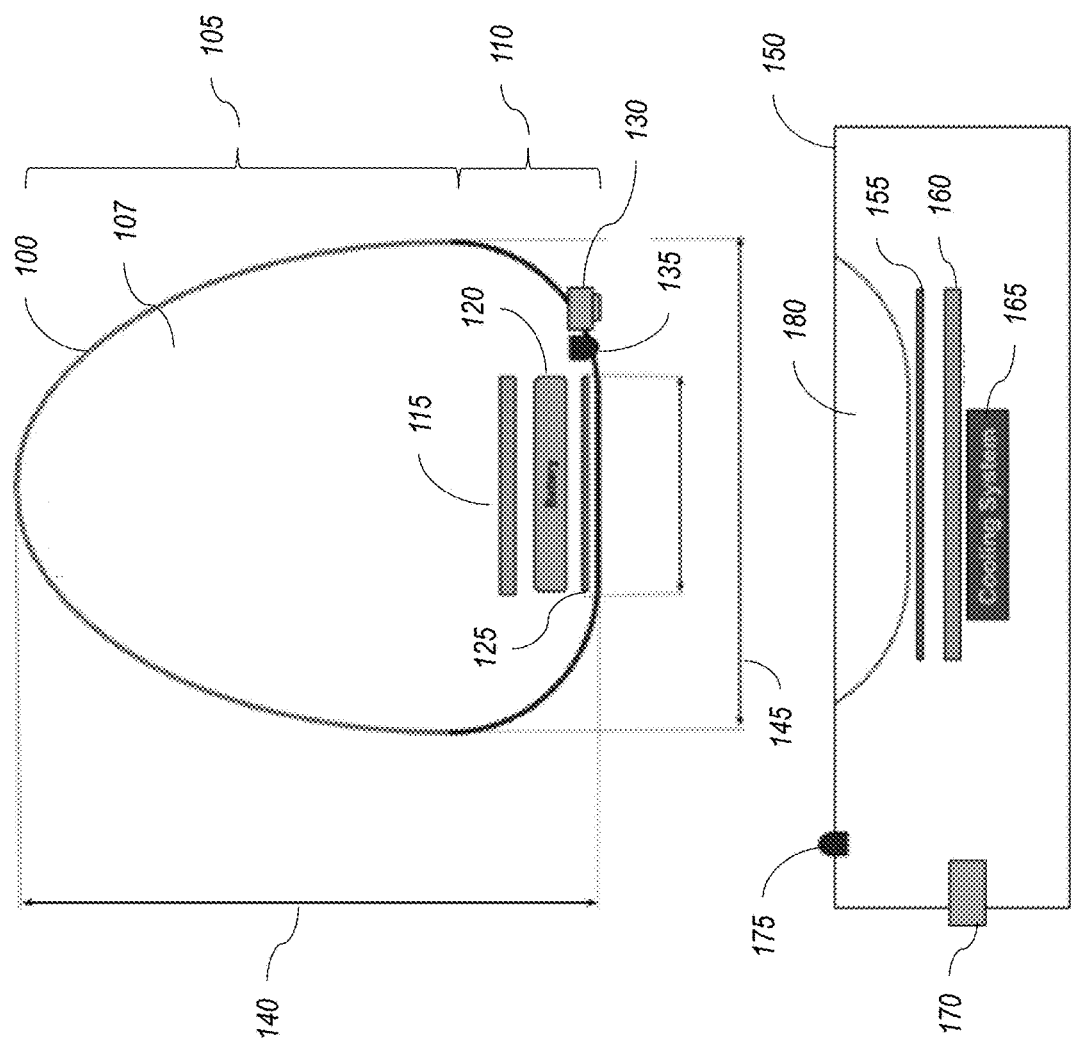
FIG. 1 illustrates a schematic of an exemplary hand device in accordance with embodiments.

FIG. 1 illustrates an exemplary schematic of a device 100 in accordance with embodiments. Shown are two portions of the device 100 and a base 150. The top portion 105 is a compressible material preferably biocompatible so that the device can be used in sterile environments such as hospitals. Top portion 105 forms a cavity 107 on the interior of the device 100. In some embodiments, components of the device 100 describe further below can lie within the cavity 107. In other embodiments, components can lie only within a cavity of the bottom portion. The bottom portion 110 is a rigid material with a flat or substantially flat facet on its surface. The bottom portion is preferably rigid to provide a stable area to mount the electronics and other internal components, to protect those components and to provide stable surface portion so it can stand upright when not in use or for mounting the device for charging or storage, for example, on the base 150 or a flat surface. Preferred embodiments of the device have an outer material that creates friction with the skin of the hand to reduce slipping from a user's hand. Preferably the flat surface is provided with a non-flexible material for stability. That is, the material of the portion of the device that includes the flat surface is preferably constructed from material that does not deform under the weight of the device when the device is resting on a surface such as a charging base. It is expected that the non-flexible portion is not a portion of the device through which force or interior pressure measurements are captured. A further advantage of a non-flexible portion is that assembly of the device is made simpler because electronics can be introduced to the interior of the device through a partition in the non-flexible portion, anchored to a substantially stationary and substantially non-deformable anchor point in the non-flexible portion.

Device 100 includes a PCB 115 for the various components and a microcontroller, discussed further below. The bottom portion 110 preferably includes a reset button 130 and LED 135. Reset button 130 can be used to reset or calibrate the one or more sensors, particularly a barometer or other pressure sensor, which are discussed further below. Prior art devices are airtight so that air pressure on the interior of the device can be properly maintained. The inventors have found, however, that designing, manufacturing and maintaining a device that need not be hermetically sealed is simpler and more cost-effective. Accordingly, reset button 130 preferably includes a valve to allow the air pressure on the interior of the device to adjust to equilibrium with the ambient air pressure. In some embodiments, a valve can be included in the bottom portion of the device that is rigid. The valve can be depressed to allow the interior air pressure to reach equilibrium by way of a valve pin on the base 150 that presses against the valve or providing a user with a valve tool for depressing the valve. When the valve is pressed against the body of the device 100, near-airtightness can be achieved, thus allowing a pressure sensor, as described further below, to operate within acceptable error bounds. In some embodiment, a valve can be located in the top portion 105

LED 135 can be used to indicate status of the device 100 including, but not limited to, battery charge level, charging state, wireless communications status or activity, power state (on/off), error status, usage mode and the like.

Also included in device 100 is a battery or power storage unit 120 and charging receiving coil 125. Battery 120 can be a lithium-ion or some other type of rechargeable battery. Charging coil 125, likewise, can be a standard charging receiving coil. Charging coil 125 is used for induction charging. In some embodiments an added port for charging can make air pressure regulation more difficult. As a result, induction charging is preferred for charging battery 120.

Device 100 preferably fits in a standard adult-sized hand. Thus, the device 100 has a height 140 at its longest of preferably about 80 mm and a width 145 at its widest of preferably 60 mm. The device should have a diameter around 6 cm. The overall weight of the device 100 is preferably in the range of 90 g to 100 g.

Figure 2:
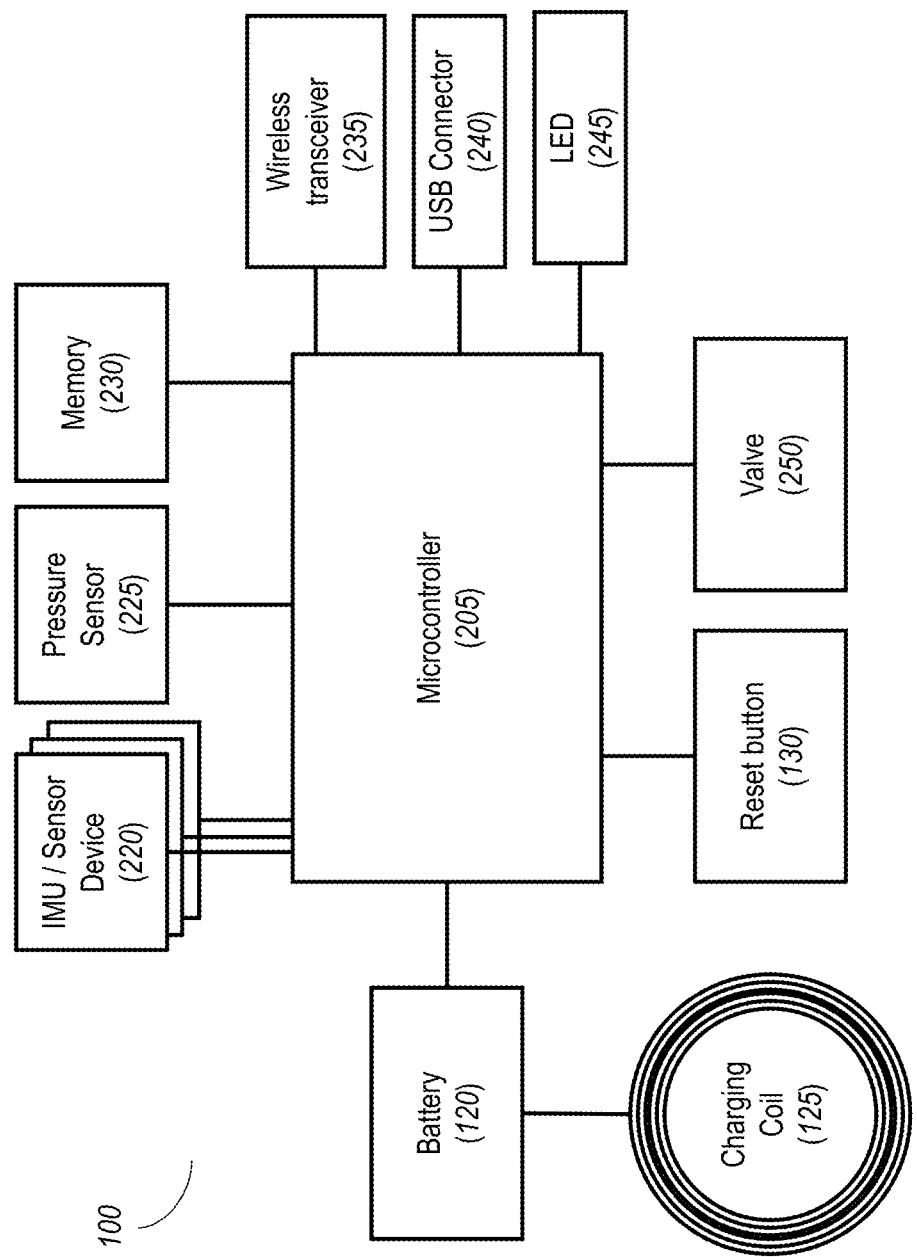
FIG. 2 illustrates a block diagram of components of an exemplary hand device in accordance with embodiments.

Base 150 preferably includes the following components wireless charging coil 155, electronics 160 for charging, a cooling system 165 to prevent overheating of the base during charging, LED 175 to provide charging status indication, and a power connector 170 for providing power for charging and LED operations. Base 150 preferably includes a hollowed volume matching the shape of the bottom portion 110 of the device 100 so that it remains stationary during charging. FIG. 2 illustrates an exemplary block diagram of a device 100 in accordance with embodiments. Device 100 includes a microcontroller 205 powered by battery 120 which is in turn charged with charging coil 125. Coupled to microcontroller 205 are various other components shown in the block diagram, preferably via PCB 115. Embodiments include one or more inertial measurement units (IMU)/sensor devices 220 for measuring orientation, position and movement of device 100. Preferred embodiments can use a sensor device such as the Physilog® from Gait Up, although other IMU/sensor devices can be used. IMUs that can be used include an accelerometer, a gyroscope, a magnetometer, and the like. A plurality of IMUs or different combinations of sensors can be used to provide tracking data with measurements of orientation, position and movement in multiple degrees or for more complex, compound movements for example, as described in U.S. patent application Ser. No. 16/172,818 which is incorporated by reference herein in its entirety or as described, for example, in connection with FIG. 10 including combining acceleration and magnetic field data from an accelerometer and magnetometer. Device 100 also includes a pressure sensor 225 coupled to microcontroller 205, such as a barometer, in accordance with preferred embodiments. Pressure sensor 225 is preferably a MEMS barometer given the preferred sampling rates, their size, cost, low power consumption, and the precision required for dexterous hand function measurement, rather than absolute grip force measurement. Pressure sensor 225 preferably measures force with a force sensitivity of <0.1N and reliability of <0.1N. Typically, the pressure inside the hand device will range from 0.7 bar to 1.7 bar. It should be understood that pressure sensor 225 can be combined with an IMU/sensor device 220 in that all of the sensors share a common housing and common electronics. For example, the preferred sensor device, the Physilog includes a 3D accelerometer, a 3D gyroscope, a barometer as well as other components described herein such as a wireless transceiver, as part of its family of sensors.

Figure 5:
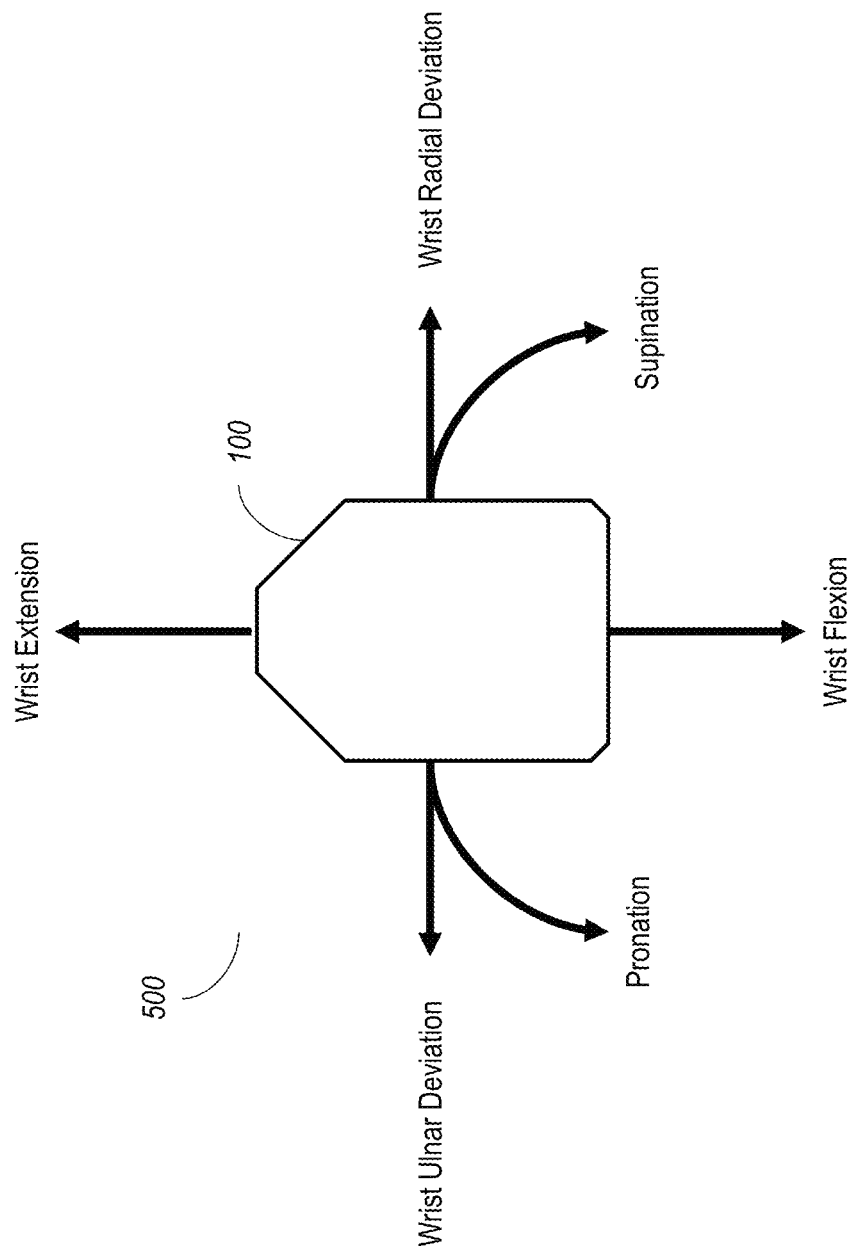
FIG. 5 illustrates a schematic of movements measured by exemplary hand devices in accordance with embodiments.

Referring to FIG. 5, an exemplary diagram 500 of movements of a device 100 measured by IMU/sensor device 220 is shown. A preferred embodiment will include at least measurement of wrist extension and flexion, wrist pronation and supination, and wrist ulnar and radial deviation. In particular, preferred embodiments will measure magnitude of displacement, velocity (which includes direction) and acceleration of the device in each of the directions indicated. Additionally, preferred embodiments will measure dexterous grasp of a user, including magnitude, velocity and acceleration of finger flexion (e.g., grip) and extension force in a pincer gesture, palming gesture, or whole-hand gesture. Gesture here refers to how the device is held in the hand. In some embodiments, the type of gesture is indicated by the activity performed by the user and, accordingly, the activity instructs the user on the gesture required.

Returning to FIG. 2, preferred embodiments can include a memory 230 for storage of computer instructions, buffering sampled data from sensor devices 220, 225, and the like. Wireless transceiver 235 can be used to transfer sampled data from sensor devices 220, 225 for analysis to an external computing device, to receive updates to software or firmware on the device, to receive instructions for executing computer instructions for adjusting power consumption, adjusting sensor sampling, operating a haptic motor, resetting or calibrating sensors, air pressure, and the like. To improve wireless connectivity, preferred embodiments will include an antenna on the upper face of the PCB 115. Some preferred embodiments can include a USB connector 240 to perform similar functions or for charging battery 120. For the same reasons that an induction charging coil is preferably used to charge a device rather than a different kind of charging port, wireless communication is preferable to a USB port.

FIG. 2 shows a reset button 130 and valve 250 as separate components. It should be understood that the reset button 130 and valve 250 can be combined so that the reset button 130 also adjusts the interior pressure to the ambient pressure when pressed.

Some preferred embodiments can further include a haptics motor (not shown) for providing haptic feedback to the user during an assessment, therapy, or other activity.

Figure 3:
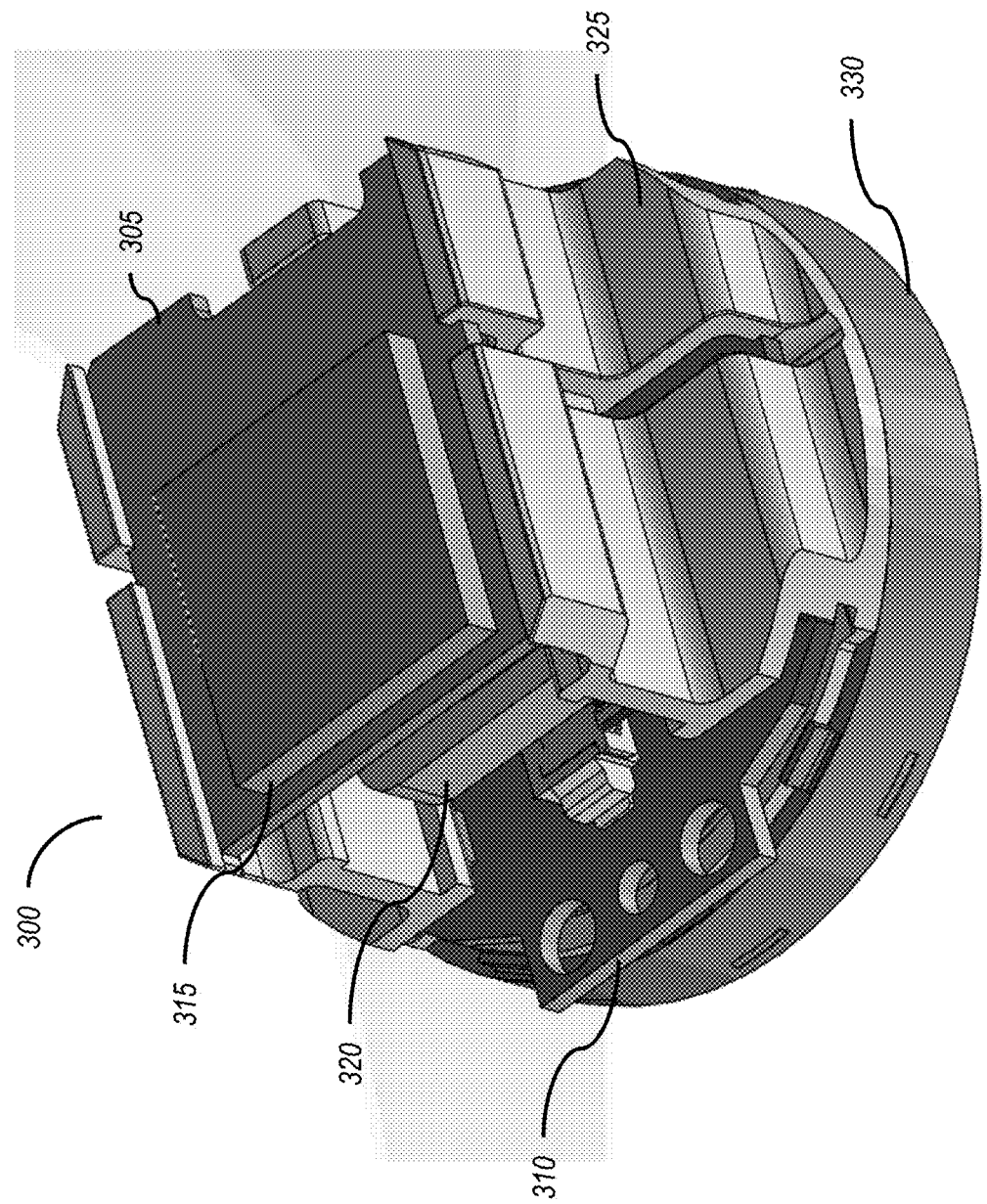
FIG. 3 illustrates components of an exemplary hand device in accordance with embodiments.

FIG. 3 illustrates an exemplary design 300 for the electronics of device 100 according to some embodiments, the design 300 can include two PCBs 305, 310. A sensor device 320 is placed on PCB 305 while microcontroller 315 is placed on PCB 310. Housing 330 contains a battery and charging coil. Structural members 325 hold the various components in place and maintain stability in relation to the device body.

Figure 4:
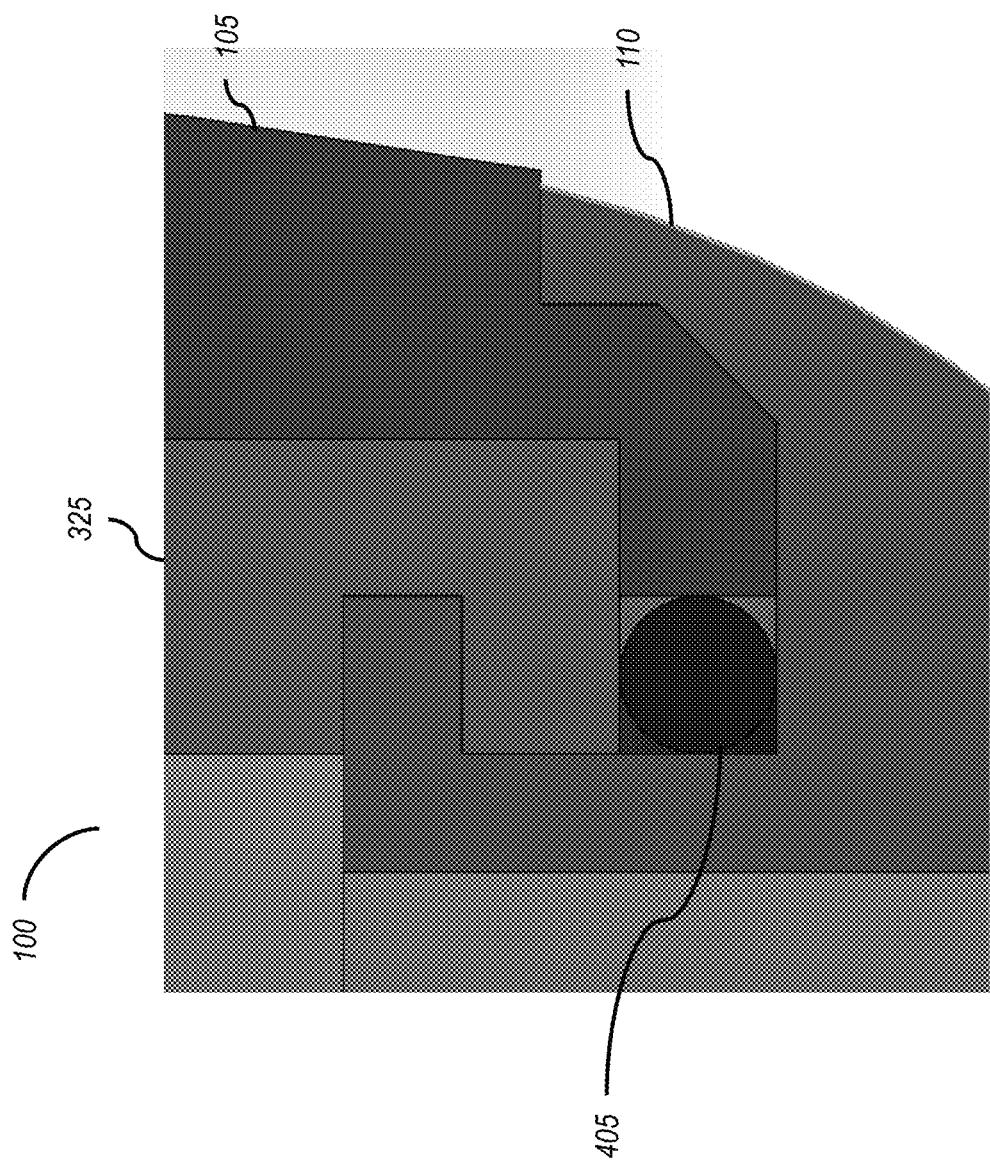
FIG. 4 illustrates a cross-section of a portion of an exemplary hand device in accordance with embodiments.

FIG. 4 illustrates an exemplary design cross-section of a device 100 in accordance with embodiments. In the figure shown the top portion 105, bottom portion 110, and housing 325 are fitted together in a jigsaw fashion with an O-ring 405 to maintain a seal at the confluence of the three components. The O-ring 405 can have different cross-section shape profiles so long as a seal is maintained. It should be understood that, as noted above, the seal is intended to be near-airtight, but non-hermetic to provide for ease and cost-effectiveness of manufacturing, repair and the like.

Figure 6B:
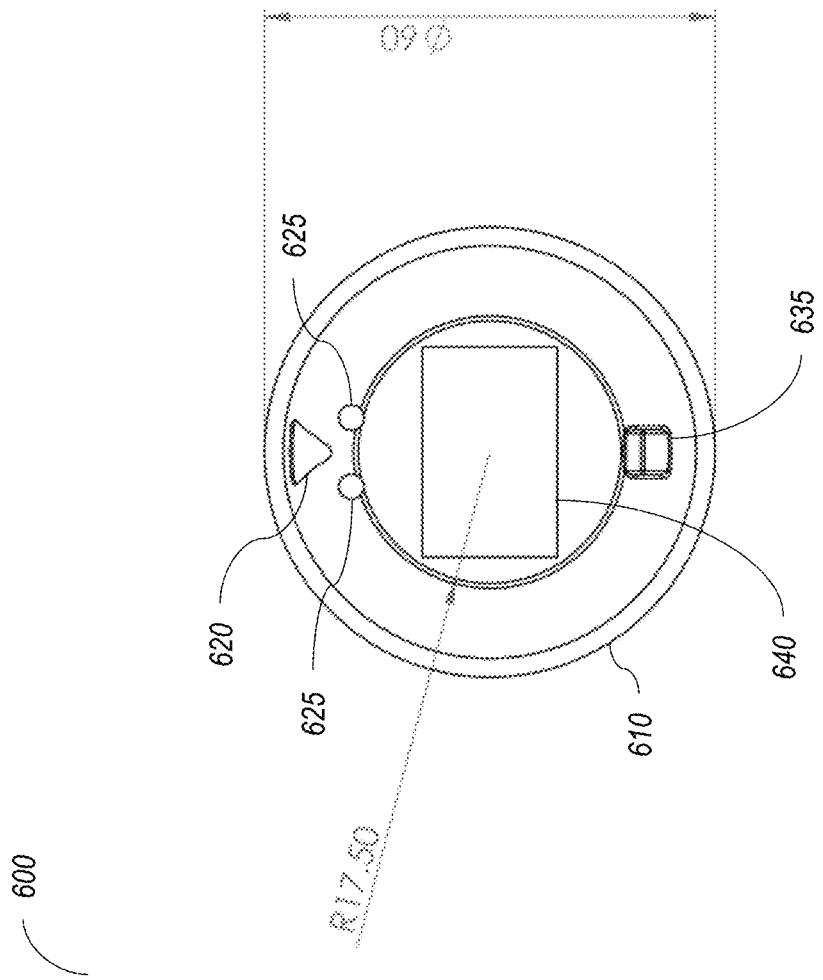
FIGS. 6A, 6B and 7 illustrate a schematics of exemplary hand devices in accordance with embodiments.
Figure 6A:
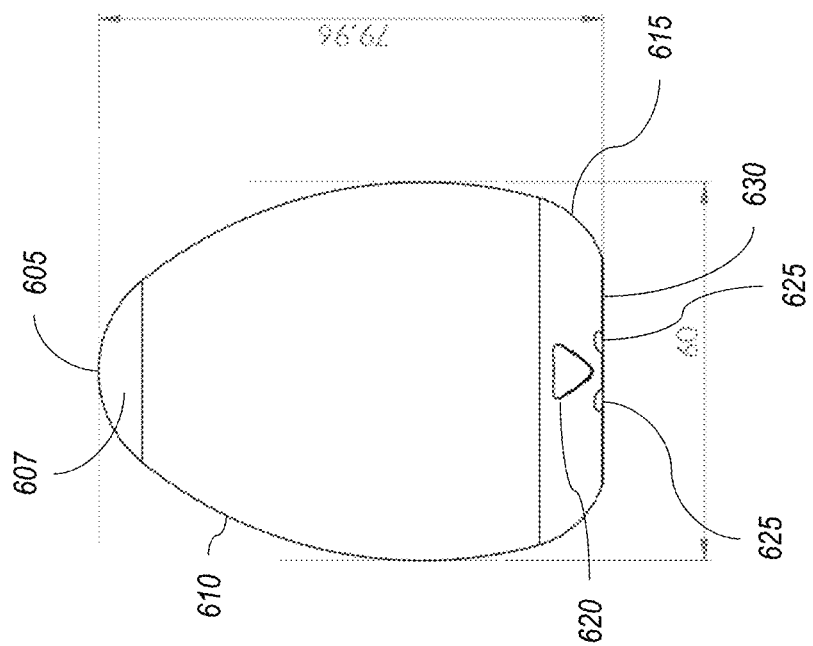

Referring now to FIGS. 6A and 6B, exemplary illustrations of a device 600 in accordance with embodiments are shown. Device 600 includes an active marker 607 for use in tracking applications. By including active marker tracking in the device along with sensor tracking accuracy of movement and position is increased. An active marker 607 can be an active marker as disclosed in U.S. patent application Ser. No. 16/524,085 which is incorporated by reference herein in its entirety. Embodiments that include an active marker can include a third portion 605 in addition to a top portion 610 and bottom portion 615 similar to the top and bottom portions as discussed in connection with FIG. 1, the third portion 605 being above the top portion 610 and housing the active marker 607. In some embodiments, the top portion 605 can include a semi-transparent or semi-opaque material such that active marker 607 can be made visible from underneath the material of the top portion 605. The active marker can be powered via the same power storage device providing power to the other components of device 600. The exemplary device 600 of FIG. 6 has a height of 79.96 mm. Device 600 also includes a reset button 620 and two LEDs

625. LEDs 625 can be used in combination to communicate status indicators described herein.

In some preferred embodiments, the device surface can include high contrasted graphical elements for possible computer vision tracking, calibration, or both, in lieu of or in combination with an active marker. Green or blue are preferrable colors for segmentation from hand detection. To the extent the device 100 or 605 includes such graphical elements, such graphical elements are preferably included on the top portion 105 or 610, respectively.

FIG. 6B illustrates the bottom face of the bottom portion 615, showing placement of the reset button 620 and LEDs 625. Also shown is a valve 635 for regulating air pressure as described herein. In preferred embodiment, the bottom portion 615 includes a sealed cover for an opening 640 to the underside so that some electronic components are reachable. In some cases, a hand device can accept a standard alkaline battery or a type of rechargeable battery, but without a charging coil and thus require access to the battery compartment.

Figure 7:
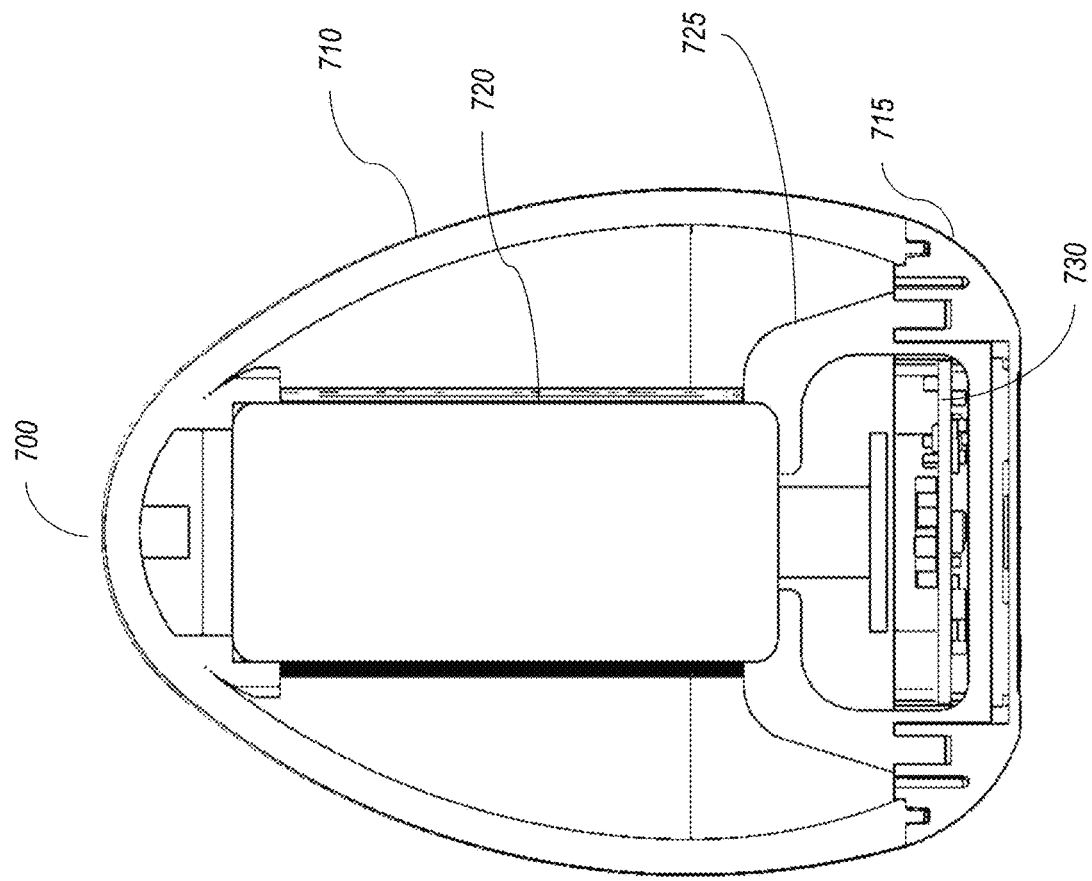

Turning now to FIG. 7, an exemplary design for a device 700 in accordance with embodiments is illustrated. Here, a sensor device 720 is oriented orthogonally to PCB 730 and is held in place via structural members 725. PCB 730 is placed horizontally along the base of the device 700.

Embodiments of hand devices described herein can allow detailed assessment of a user's dexterity via simple, lightly gamified activities designed to output accurate metrics of performance Such activities can be provided by the therapy platform described above.

Figure 8:
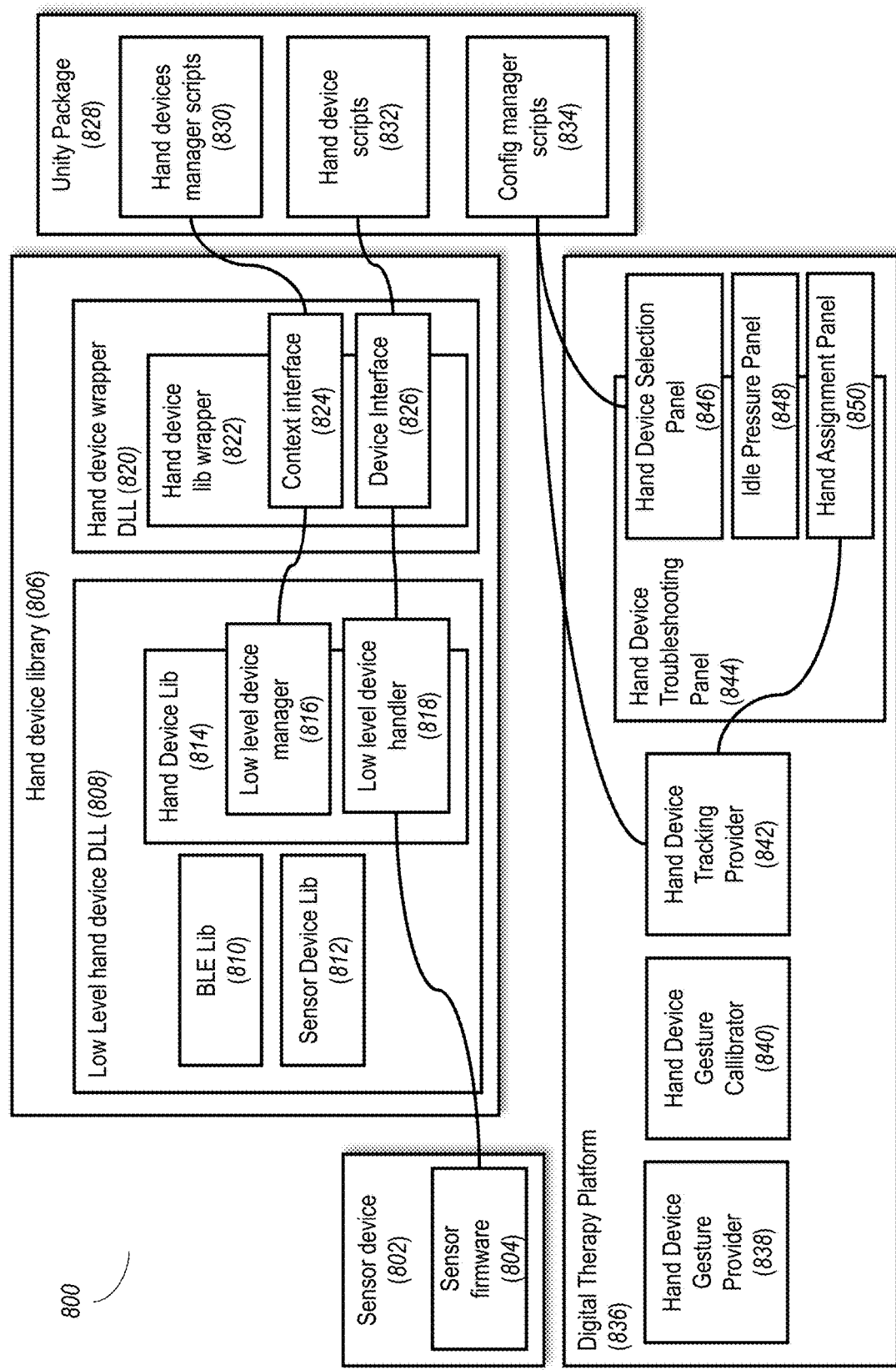
FIG. 8 illustrates a block diagram of an exemplary architecture in accordance with embodiments.

Hand function assessment, training and therapy, including finger individuation and dexterous grasping, for hemiparesis and other conditions using embodiments of the device described above is useful in the context of a larger digital therapy platform. Such a digital therapy platform can include serious games for training and therapy and assessment activities. One such a digital therapy platform is the MindMotion™ platform from MindMaze SA. FIG. 8 illustrates a block diagram of an exemplary architecture 800 for integrating hand function devices as described herein with such a digital therapy platform. It should be understood that the architecture presented is applicable to a PC computing environment. Those of ordinary skill in the art understand how a similar architecture in other computing environments, operating systems or platforms would be organized.

A hand device library 806 preferably includes two run-time libraries. The low level hand device DLL 808 includes a BLE lib 810, for hardware/OS abstraction for low level access to wireless communication services, e.g., Bluetooth; a sensor device lib 812 for generic sensor device communication protocol and configuration methods; and a hand device lib 814 for configuration and setup specific to the hand device. In the embodiment illustrated, the low-level device handler 818 is in communication with the sensor firmware 804 to handle connection and streaming with the sensor device 802. In preferred embodiments, streaming data parameters can be set on connection. Streaming data parameters can include selection and configuration of packet content, including timestamp data, acceleration data, gyroscope data, barometer data, temperature data, pressure/force normalization data, quaternion data, and various calibration parameter data for IMUs, including accelerometers, gyroscopes, and the like. Calibration parameter data can include gain, offset and scale. It should be understood that packet contents should be configured according to the sensor devices used in the hand device connected. The other run-time library, the hand device wrapper DLL 820 includes a wrapper for the hand device lib 822 interface. Accordingly, the context interface 824 provides an interface for the low-level device manager 816 and the device interface 826 provides an interface for the low level device handler 818.

Unity Package 828 includes software components including hand devices manager scripts 830, hand device scripts 832, and config manager scripts 834. The hand devices manager scripts 830 creates game and activity objects when a hand device is discovered and handles messaging communication generally with the hand devices through the context interface 824. Hand devices scripts 832 provides configuration and data management for an individual, identified hand device through the device interface 826. The config manager scripts 834 provides startup and live configuration of a set of hand devices by automatically discovering, connecting and streaming when necessary. Unity is a preferable scripting tool appropriate for the exemplary architecture 800 and it should be understood that other development platforms can be used.

The exemplary digital therapy platform 836 shown includes unity scripts in a hand device gesture provider 838, hand device gesture calibrator 840, hand device tracking provider 840, and a hand device troubleshooting panel 844. The providers 838, 840 and 842 provide services for their respective activity functions (i.e., calibration, tracking, etc.). For example, tracking provider 840 provides device tracking capabilities for activities and games (not shown) in the digital therapy platform 836. The troubleshooting panel 844 provides services for fixing connections, hand assignment for devices, and fixing reset issues for hand devices. In the embodiment represented, the troubleshooting panel 844, includes a hand device selection panel 846, idle pressure panel 848, and a hand assignment panel 850 to provide those and other services. For example, the selection panel 846 can communicate with the config manager scripts module 834 to ensure a sufficient number of devices are streaming for the current activity in the platform 836. The idle pressure panel 848 captures the air pressure of a hand device while idle. The hand assignment panel 850 can assign a left or right hand to a device for the hand device tracking provider 842.

Figure 9:
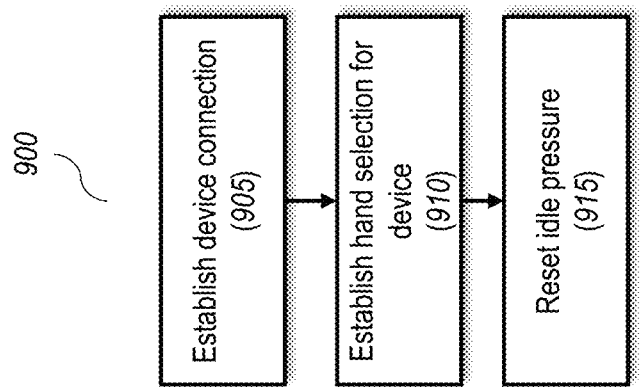
FIGS. 9-13 illustrates a flowcharts of exemplary methods of operation of a hand device in accordance with embodiments.

The architecture described in connection with FIG. 8 is exemplary and applies to some preferred embodiments. Additionally, the components and their organization are illustrative, and they can be further separated or combined in accordance with embodiments. In some embodiments, some components can be implemented using different technology. For example, Windows-based components and Unity, which is a commonly-used development platform, are described in the exemplary architecture of FIG. 8, but other platforms can be used and those of skill in the art can understand how target systems other than Windows can support embodiments FIG. 9 illustrates a flowchart 900 of a method for initiating a hand device for use with a therapy platform in accordance with embodiments. In step 905, a connection to a hand device is established. In some embodiments a connection to a hand device can be made according to a known wireless protocol, e.g., Bluetooth, for establishing a connection with a peripheral. In step 910, a hand selection indicator is selected for the device. The device is assigned to either a left or right hand so that tracking is accurate for the therapy platform activity. In some instances, an activity will call for the use of two hand devices, each of which can need to be assigned to a specific hand. In yet other cases, an activity can call for more than one user, each using one or two hand devices. Accordingly, a plurality of hand devices can be assigned to the same hand side (i.e., left or right). Such assignment is important so that particular movements can be measured properly such as wrist pronation and supination, wrist extension and flexion, and the like. In some embodiments, this step can be performed by simply receiving an instruction having a hand-side indicator which can be generated from manual user input or from detection of specific movements. For example, an instruction to request a wrist extension, or some other movement, can be sent to prompt the user to move the hand device using that movement. The sensor data indicating the direction of movement or displacement of the device can reveal which hand is being used; and the hand-side indicator can, thus be determined.

At step 915, the idle pressure of the device is reset. In preferred embodiments, the air pressure of the hand device is captured from a barometer reading when the hand device is not in use or in the grasp of a user. As noted above, preferred embodiments of the hand device are non-hermetic and, thus, the air pressure is likely to differ from one use to the next. Thus, the internal air pressure is preferably read to establish a baseline prior to commencement of an assessment or therapy exercise.

Figure 10:
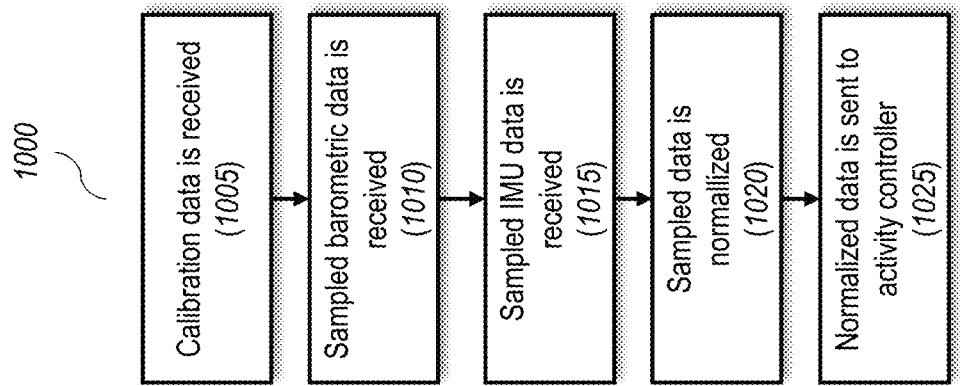

FIG. 10 illustrates a flowchart 1000 of a method for providing hand device sensor data for use in an activity in a therapy or other platform. At step 1005, calibration data is received. In preferred embodiments, data for user range of motion, maximum pressure for gestures, minimum and maximum acceleration, and the like are received from a calibration process during which the user performs certain movements, grips and the like. The calibration data is retained in a data store, for example, a memory such as in Figure X, for later retrieval during an activity. Range of motion calibration is typically made in world space, not in local space. As an example, range of motion data can be determined from accelerometer data. For wrist flexion/extension, a plane is derived from an acceleration vector when the device is at maximum flexion and one when it is at maximum extension. The angle between these two vectors on the plane then can give the range of motion in degrees. At step 1010, raw sample barometric data is received. At step 1015, raw IMU sensor data is received. The raw data for each of these steps preferably includes timestamp data. It should be understood that the sensor data received can be from one or more different sensors of the same type, different type, or a combination thereof. For accelerometer data, preferred embodiments include a signal processing to dampen the signal with minimal impact on latency for use during calibration and activity use.

Embodiments of the present invention can be used to measure and track complex, compound movements based on accelerometer readings. For example, a movement involving yaw measurement from acceleration data is not possible without having a corresponding measurement of gravity in a device in typical devices. Such a movement involves, for example, wrist extension while holding the device as it rests along a flat surface (e.g., a table). Using an advanced gyroscope can provide readings to create controller data for an activity. The inventors have found that combining measurements from an accelerometer with magnetometer readings can be used as well to maintain an overall lower cost device.

The state of the art to compute the orientation of a device from an IMU is by using mainly the gyroscope signal. In practice, however, gyroscope signals have an inherent drift, the amount of which is highly dependent on the sensor. This drift can lead to an incorrect orientation reading after a few minutes and, therefore, can require frequent recalibration by the user. Even the best gyroscope-derived quaternion in the state of the art has drift of a few degrees per minute Accordingly, in some preferred embodiments an accelerometer reading can be more appropriate for some activities, particularly serious games where the hand device is used as an activity or game controller. Accelerometers generally give a drift-free signal, but an accelerometer gives information about just two axes, pitch and roll. The pitch and roll are computed assuming that the device is static, any movement with an acceleration will have an impact on the computed orientation. Preferred embodiments, therefore, project the current acceleration vector on this plane and compute the angle between the projection and one of these two vectors to give the current position. As a result, most of the "jerkiness" is mitigated. The filter can be tuned according to needs for certain activities with a trade off with latency.

At step 1020, the raw data is normalized. This step preferably uses data about which hand, which user, the type of gesture (e.g., the type of grip used), calibration data, and other configuration data to normalize the data into values useful for an activity. In some instances, normalization can include increasing magnitude of values of some of the data in relation to other data based on a user's range of motion. The user's range of motion parameters can be received from, for example, step 1015 during which the user is prompted to perform certain movements, grips, etc. For example, the magnitude of finger flexion can be increased in relation to wrist flexion where the user's finger range of motion is reduced but wrist range of motion is not so that an finger flexion appears more sensitive in the context of an activity. Preferred embodiments can also normalize pressure data against temperature readings from the interior, exterior or both of the device in cases where the pressure sensor does not already compensate.

At step 1025, normalized data is sent to an activity controller that is part of a therapy or other activity platform. For example, in preferred embodiments the normalized data can be sent to a hand device gesture provider 838 (for pressure data), hand device tracking provider 842 (for IMU data). Other types of activity controllers can receive normalized data depending on the type of activity platform.

Figure 11:
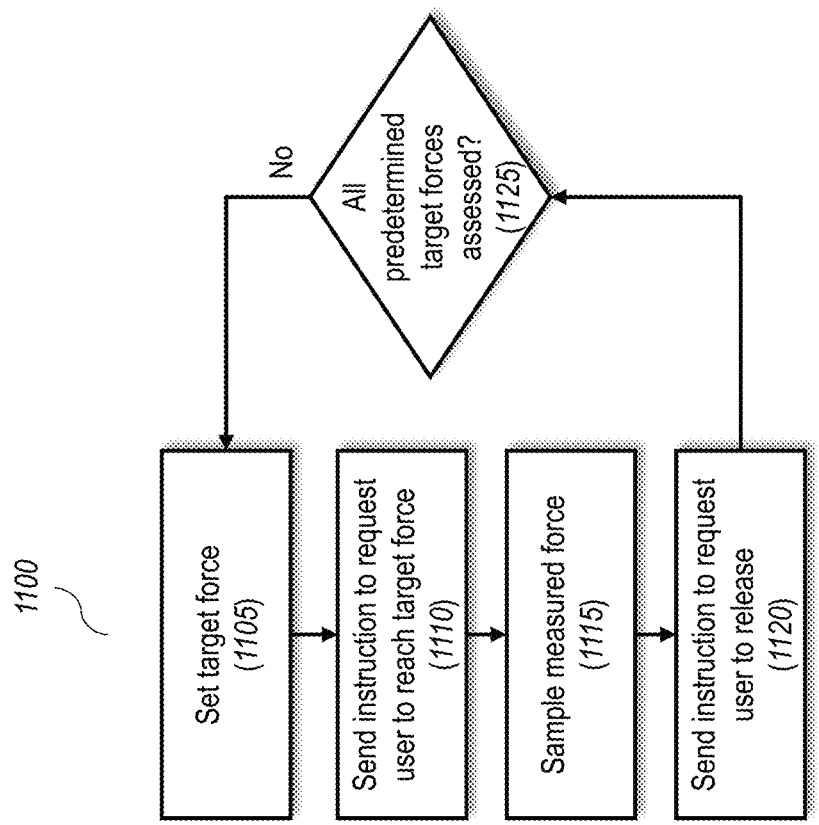

FIG. 11 illustrates a flowchart 1100 of a method of assessment for grasp and release measuring force. At step 1105, a target force is determined against which the user's grasp is tested. At step 1110, an instruction is sent to provide a prompt to the user to begin applying force to the device. In preferred embodiments, the user is requested to apply the force for a determined amount of time. When instructed, the user squeezes the device to reach a measured force, maintain that force for a short period at the target force, then completely release it. In such cases, the force applied by the user is measured by way of detecting changes in the barometric pressure of the interior of the device, for example at step 1115, so that it can be determined whether the user was able to reach the force and how well the user was able to maintain the force over the amount of time. The metric from this assessment is a function of the delta between the force applied and the target force. This metric provides information on the range of forces within which the patient is able to accurately grasp and maintain his grip. At step 1120, an instruction is sent to provide a prompt to the user to release the grip. At step 1125, the process is repeated for a range of target forces. In some cases, the range of target forces can include only one target force. In other cases, the activity assesses this through a large range of forces, from gripping the device very lightly to squeezing it tightly.

Figure 12:
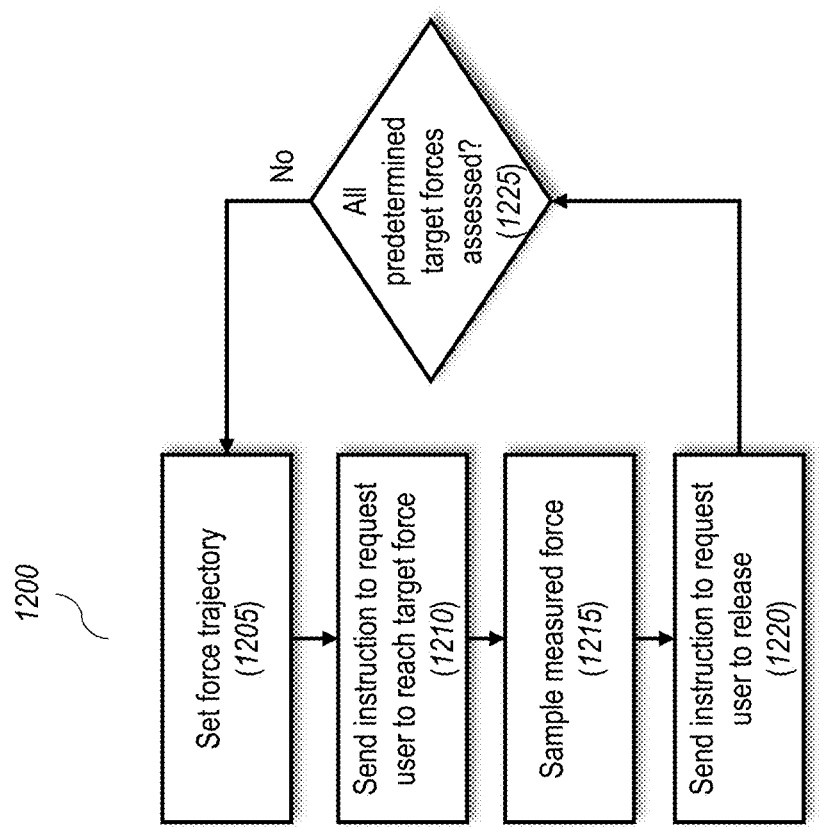

FIG. 12 illustrates a flowchart 1200 of a method of assessment for grasp and release measuring modulation. At step 1205, a target force trajectory is set. The assessment calls for the user to regulate the force applied to the device in order to follow a trajectory. The assessment trajectory can include target forces that form a sinusoidal or some other waveform when plotted on a y-axis against a time x-axis or that are irregular or random. At step 1210, an instruction is sent to provide a prompt to the user to begin applying force to the device. At step 1215, the barometric pressure is sampled as the target force changes along the trajectory. At step 1220, an instruction is sent to provide a prompt to the user to release the grip and end the assessment. The assessment metric is a function of the delta between the trajectory that the player traces by squeezing/releasing the device and the target trajectory. Target trajectories will have regions where the patient will have to modulate grasp with varying frequency and amplitude. This provides a measure of how accurately the patient can modulate his grasp force as a function of force applied and grasp/release frequency.

Figure 13:
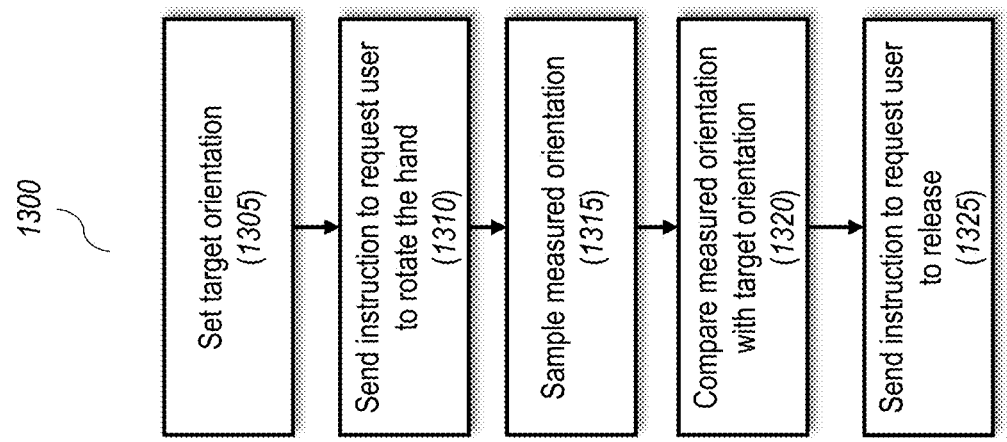

FIG. 13 illustrates a flowchart 1300 of a method of assessment for pronation and supination. At step 1305, one or more target orientations are determined. At step 1310, an instruction is sent to prompt the user to rotate a hand while holding the device. According to preferred embodiments, the user would rotate the device as instructed, using pronation and supination of the hand. At step 1315, the orientation of the device is sampled from the IMU. At step 1320, the orientation is compared with the target orientation. The angular delta between both orientations throughout the assessment will be used as a measure of the patient's ability to accurately pronate/supinate the wrist throughout a range of rotational amplitudes and speeds. At step 1325, an instruction is sent to prompt the user to end the assessment. Again, the steps from step 1310 can be repeated for additional orientations. In preferred embodiments, the sample orientation data is used generating user interface elements, for example, on a monitor or in an AR/VR environment to assist the user in reaching the target orientation.

In each of the methods described above and generally during use of the device, a sampling rate of at least substantially 60 Hz is used for both IMU and pressure sensor. More preferred is a sampling rate of substantially 100 Hz for both IMU and pressure sensor. Most preferred is a rate of 120 Hz. Sampling rates can differ for the IMU and pressure sensor, however. In some preferred embodiments, the sampling rate can be decreased for a sensor during use cases where the sensor readings are less critical. For example, in cases where the device is used to measure primarily force metrics, but not orientation, the IMU sampling rate can be throttled. Additionally, sampling rate can be throttled to conserve power, either automatically or based on a user setting.

The methods described above in FIGS. 11-13 can be combined in some preferred embodiments, for instance having to modulate one's grasp while also performing pronation/supination. That is, some exemplary embodiments include a method tracking hand and wrist movements with dexterous hand function metrics simultaneously using markerless tracking or IMU sensor data and pressure data.

The assessment methods describe above can allow each patient to be represented as a point in a multi-dimensional "impairment space," with coordinates corresponding to the score associated with each metric. For example, one of the axes might correspond to "low-force grasp-and-release accuracy score." Collecting representative data on healthy subjects will allow the identification of a "healthy cluster" within this space (corresponding to the typical scores across all assessments of healthy subjects). The patient's impairment can then be quantified as a function of the distance between his location in impairment space and the centroid of the healthy cluster.

Furthermore, the assessment methods can be used longitudinally in order to track a user's recovery or progress through a change of position in impairment space, quantifying the efficacy of a user's therapy plan as a function of how quickly the user's location approaches the healthy cluster.

Figure 14:
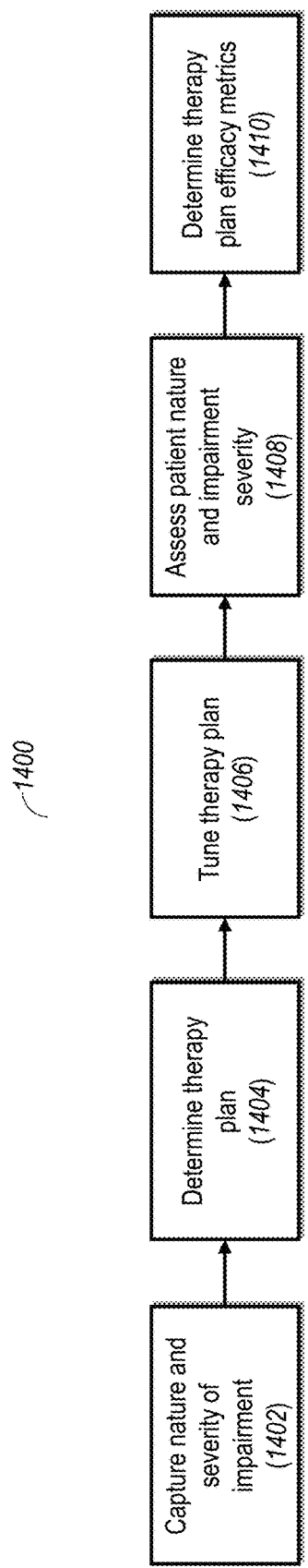
FIG. 14 illustrates a flowchart for an exemplary method of assessment and therapy in accordance with embodiments.
Figure 15A:
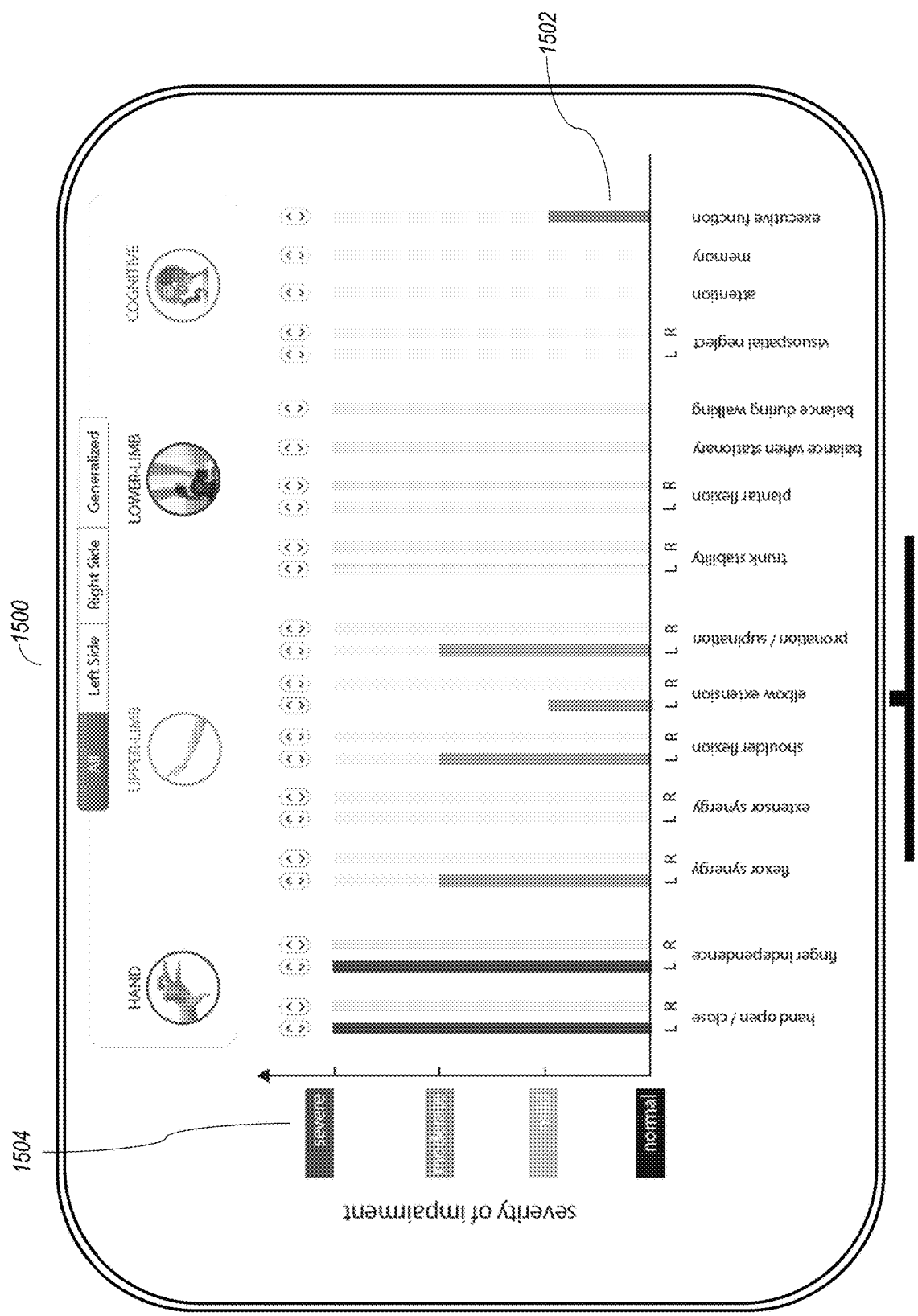
FIGS. 15A and 15B illustrate a user interfaces of an exemplary system of assessment and therapy in accordance with embodiments.
Figure 15B:
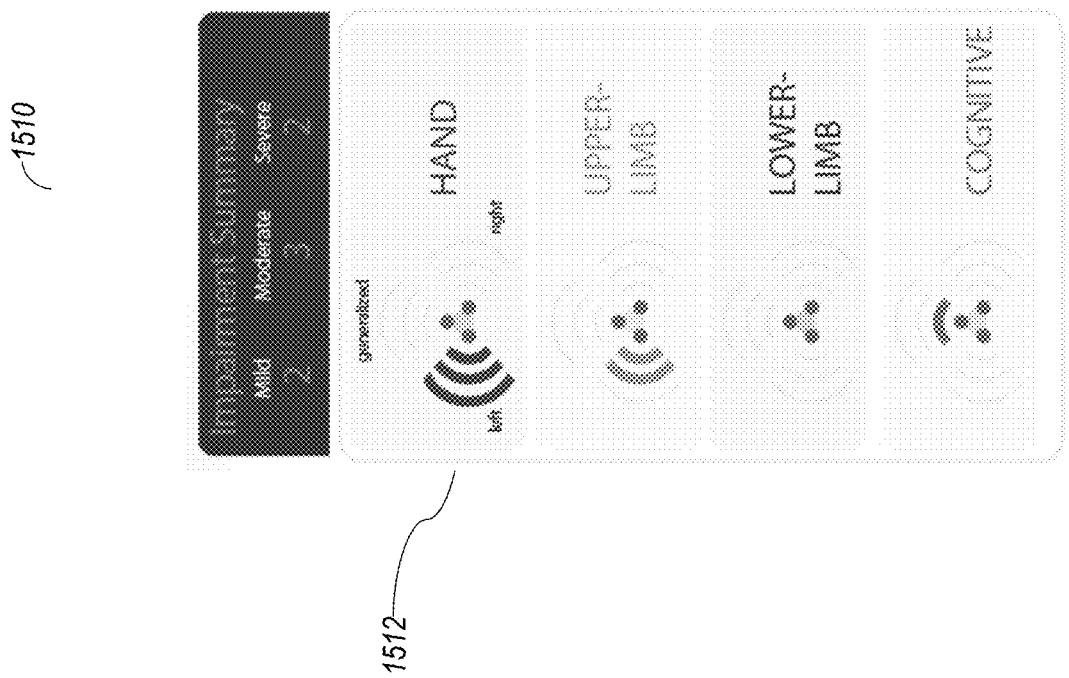

The hand device disclosed herein as well as other devices whether or not known or state of the art device are particularly useful in an assessment and therapy context as described below. For example, FIG. 14 illustrates an exemplary flowchart 1400 for a digital therapy protocol in accordance with embodiments. At step 1402, the nature and severity of a patient's impairment are captured. A therapist registers a new patient in MindMotion. The system can request that the therapist rank a patients' severity along a set of predefined measures of clinical impairment. On a macro-level, these impairments can correspond to behavioral functions (e.g., hand, upper-limb, lower-limb, cognitive, and the like). These functions, in turn, can be composed of fine-grained measures of impairment. In some embodiments, the system can accept measures input by the therapist. In some embodiments, the measures can be determined through an automated assessment process that corresponds to step 1408. The system can incorporate a user interface for the input and display of such measures, as in FIG. 15A, which illustrates an exemplary input and display user interface on display device 1500. The user interface includes values 1502 for fine-grained functions which can include, but is not limited to, such functions as hand open/close (left and right hand) and finger independence (left and right hand) for hand; flexor synergy (left and right upper limb), extensor synergy (left and right upper limb), shoulder flexion (left and right upper limb), elbow flexion (left and right upper limb) and pronation/supination (left and right upper limb) for upper limb; trunk stability (left and right lower limb), plantar flexion (left and right lower limb), balance when stationary and balance during walking for lower limb; and visuospatial neglect (left and right side), attention, memory and executive function for cognitive. The values 1502 can be based on a scale 1504. FIG. 15A shows a four-value scale of normal, mild, moderate and severe although other scales can be used which are well-known to those of ordinary skill in the art. FIG. 15B illustrates another exemplary user interface 1510 for input and display of impairment assessment measurements. Measurement values are illustrated and can be set graphically using, for example, intensity bars 1512 as shown that depict both the value and side affected. In the user interface 1510 the scale used includes values mild, moderate and severs. It should be understood that impairments and/or functions and scales other than those shown can be used in some preferred embodiments.

As the impairment features are automatically or manually populated, a macro-level summary of the patient's nature and severity of impairment is visualized for display as a user interface for a therapist or other user (e.g., a patient). In preferred embodiments, the system presents other options for the therapist to define or further customize a therapy plan. For example, the system can receive start and end dates of the patient's visits or sessions, the average time per therapy session and the like. Embodiments can then use this information as input to customize a therapy protocol or generate recommendation data for a therapy protocol.

Figure 16:
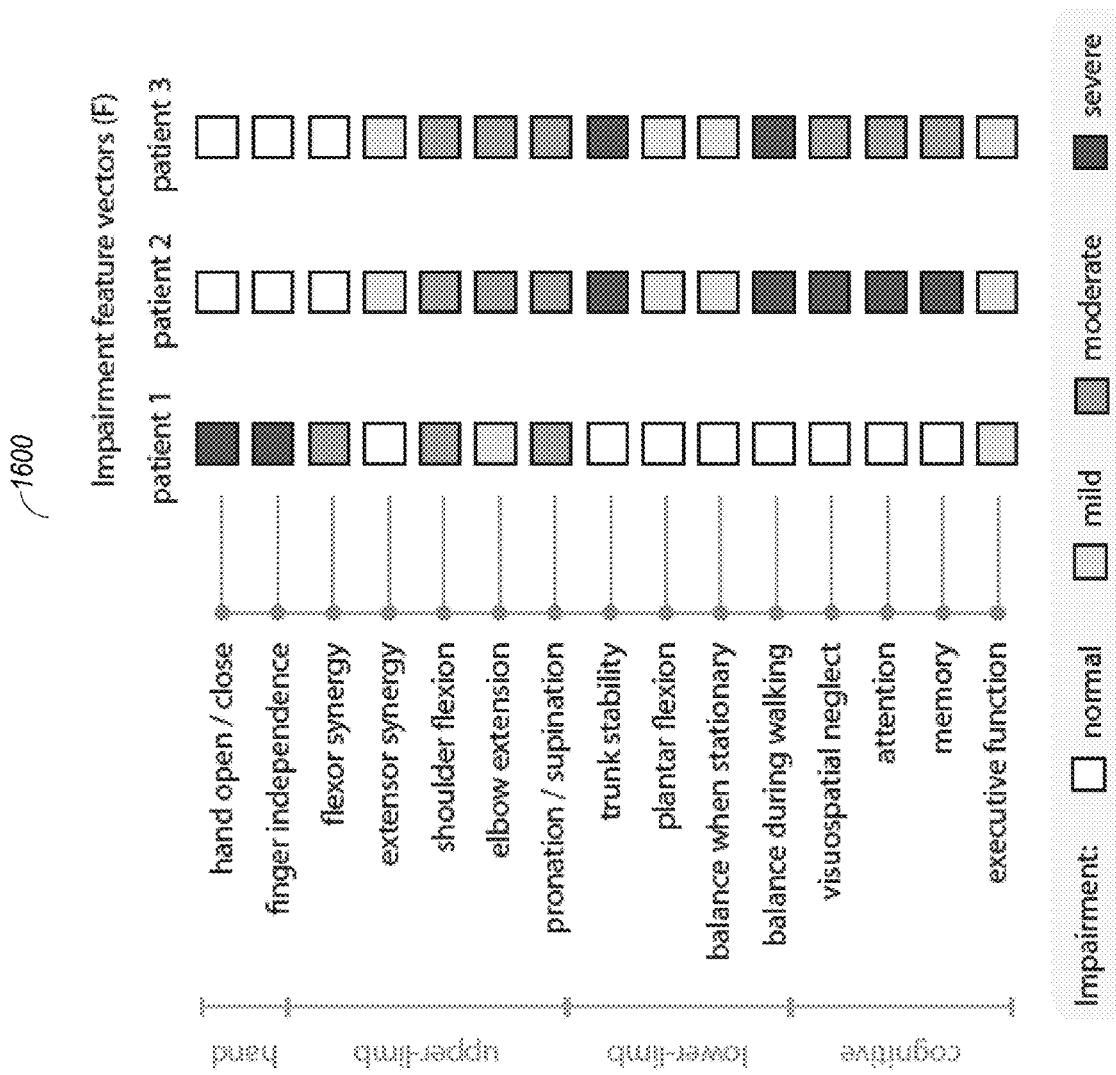
FIG. 16 illustrates various impairment function vectors in accordance with embodiments.

Referring now to FIG. 16, an exemplary illustration of impairment function vectors for different patients is shown.

Each patient has a function vector profile comprising multiple functions with a scale value for each dimension in the vector. In some embodiments, a vector can include null values for functions that are not assessed. In other words, some preferred embodiments can accommodate assessment data or measurements from a subset of the functions that the system can accommodate. Behind the scenes, a patient's impairment and severity can now be represented as a mathematical impairment feature vector (F). Impairment feature vectors for two patients might look very distinct (patient 1 vs. 2) or very similar (patients 2 vs. 3). Some preferred embodiments will generate different treatment plans for distinct feature vectors, (patients 1 vs. 2) and similar treatment plans for patients with similar feature vectors (patients 2 vs. 3).

Returning to FIG. 14, at step 1404, a therapy plan in determined. The idea is to provide the best therapy plan prescription for a patient based on his/her nature and severity of impairments. As described above in relation to step 1402 or below in relation to step 1408, a therapist enters metrics or a patient performs a multi-modal assessment which results in a vector of the patient's impairment F(f1, f2, . . . , fn) for a particular function. Each component fi contains the impairment level associated: normal, mild, moderate or severe. In preferred embodiments, a holistic multi-modal assessment is performed to generate a richer set of metrics than is available in the current state of the art. Current assessment and therapy techniques treat functions such as those discussed herein as unrelated in that functions are assessed and treated independently. For example, a peg board test is a common assessment tool intended for hand function impairment. The nine-hole peg test can be affected by upper limb and cognitive impairments. Moreover, the nine-hole peg test fails when used repeatedly for a patient because the patient adapts cognitively and can use compensatory movements to improve rather than isolating hand function. Even if such a test is biased in favor of the intended function, the extent of bias is unclear, particularly across patients and even from session to session for the same patient. The same phenomenon exists in therapy. That is, a therapy is nominally aimed at a function but affects other functions, perhaps to the detriment of the nominally aimed function. Similarly, a therapy can be nominally aimed at multiple functions but is biased towards only a subset of the functions. The impairment vector groups functions quantifies the patient's impairments so that proper therapies can be determined taking into account the biases of both the assessments and therapies used by the therapist.

The goal is then to suggest an optimal therapy plan matching the patient's impairment vector by using a combination of pre-defined "digital therapies." In preferred embodiments, digital therapies can include activities performed by patients that correspond to known exercises. In some cases, a digital therapy can include an exercise that isolates a function to optimally remove bias towards other functions. In some cases, a digital therapy can include an exercise that targets specific co-occurring impairment types (e.g., mild hand open/close+pronation/supination deficit). Each digital therapy can be either a single gamified activity or a set of activities taken from the activity catalogue. In preferred embodiments, a digital therapy is associated with a vector P(p1, p2, . . . , pn) where each component pi can be a scale value as described herein.

A linear regression is performed in order to find what is the best combination of digital therapies for each patient using vectors Pi based on his/her impairment vector F. Various linear regression models could be used to determine the relationship between the impairment vector F and the optical therapy vectors Pi such as a least squares regression analysis. Once the optimal combination of digital therapies is identified, a decision is made on the number of digital therapies to combine in the treatment plan as well as rating the order of importance (e.g., severe hand impairment is the primary focus and then moderate subluxed shoulder). This decision is based on the highest weights β derived from the linear regression, the severity of the impairment addressed by the therapy plan and medical information of the patients (e.g., condition, time of onset, pain and the like). An optimal therapy therefore can be derived by the following:

$$\text{patient impairment vectors}(F) = \beta \times P \quad (1)$$

$$\text{optimal therapies}(\beta) = (P^T P)^{-1} P^T F \quad (2)$$

Some preferred embodiments allow a therapist or other user to input schedule and dosage (i.e., duration of session and the like) data. In some cases, schedule and dosage data can be determined from modeled data from, for example, step 1410. In other cases, schedule and dosage data can be set to standard or generally accepted values from guidelines or the current state of the art. Other factors can include the patient condition or insult (e.g., stroke, TBI, etc.), age of the conditions (e.g., number of years/months, chronic/acute, etc.), a severity level, number of relapse episodes (e.g., for multiple sclerosis), and the like. Those of skill in the art can appreciate various factors that could be used to adjust schedule, dosage or both.

Figure 17:
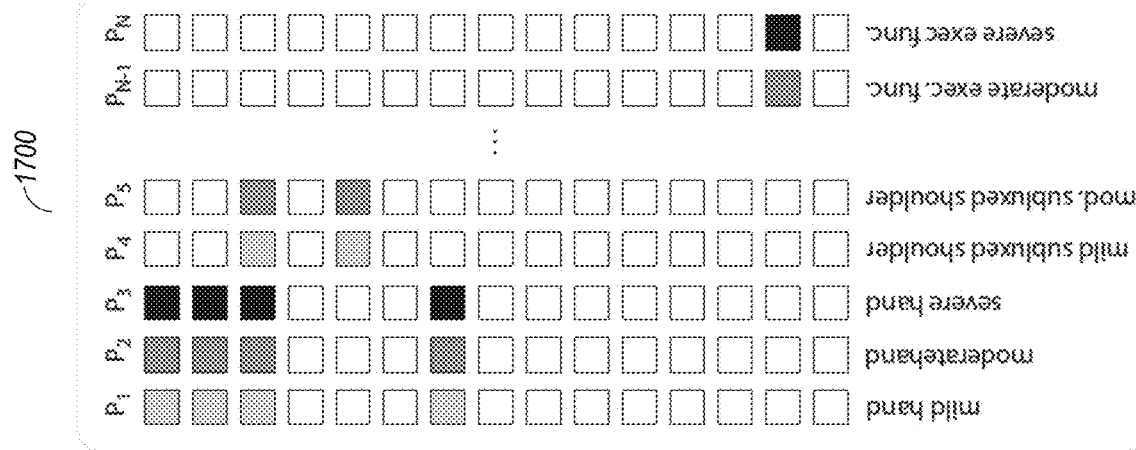
FIG. 17 illustrates a predefined digital therapies with scale values in accordance with embodiments.

FIG. 17 illustrates an exemplary set of predefined digital therapies with scale values. As shown, each therapy substantially mirrors the structure of an impairment vector in that each function within a therapy is assigned a scale value. In preferred embodiments, the scales for the impairment vector and the therapy vector are identical although some embodiments can accommodate different scales wherein a correlation between the scales is defined. These protocols are defined either by scientific literature or have been identified by experts in the field (therapists/neurologists), and usually target specific co-occuring impairment types (e.g. mild hand open/close+pronation/supination deficit). The system then estimates the combination of protocols that best explain the patient's impairment prole. The identified combination of digital therapies, coupled with a suggested schedule and dosage is then the recommended therapy plan for the patient. In the example shown, digital therapies $P_2$ and $P_4$ could correspond to patient 1's impairment vector and, accordingly, by prescribed to patient 1.

In preferred embodiments, the optimal digital therapies are then used to determine the activities or exercises to prescribe to the patient. Activities that are appropriate for the patient for the digital therapies are identified and selected. In some cases, activities, which can be task-based and functional, are developed with a single therapeutic goal in mind. Thus, it is straightforward to identify a set of activities from within a set of predefined activities that are appropriate to train the specific impairment features (e.g., activities that train severe hand and moderate subluxed shoulder impairments for patient 1 from FIG. 16). In some preferred embodiments, each of the digital therapy plans within the system can have a predefined therapy plan structure of activities versus rest phases, that the chosen activities can then slot within. FIGS. 18, 19 and 20 illustrate an exemplary catalog of activities, a therapy plan structure and detailed view of a therapy plan structure, respectively.

Figure 21:
FIG. 21 illustrates a user interface view of recommended digital therapy plans in an exemplary system of assessment and therapy in accordance with embodiments.

FIG. 21 illustrates an exemplary user interface view of recommended digital therapy plans. Preferred embodiments determine a match level for each therapy with respect to the patient's impairment vector. The match level indicates the correspondence derived from the algorithm for determining the optimal therapy plan.

Figure 22:
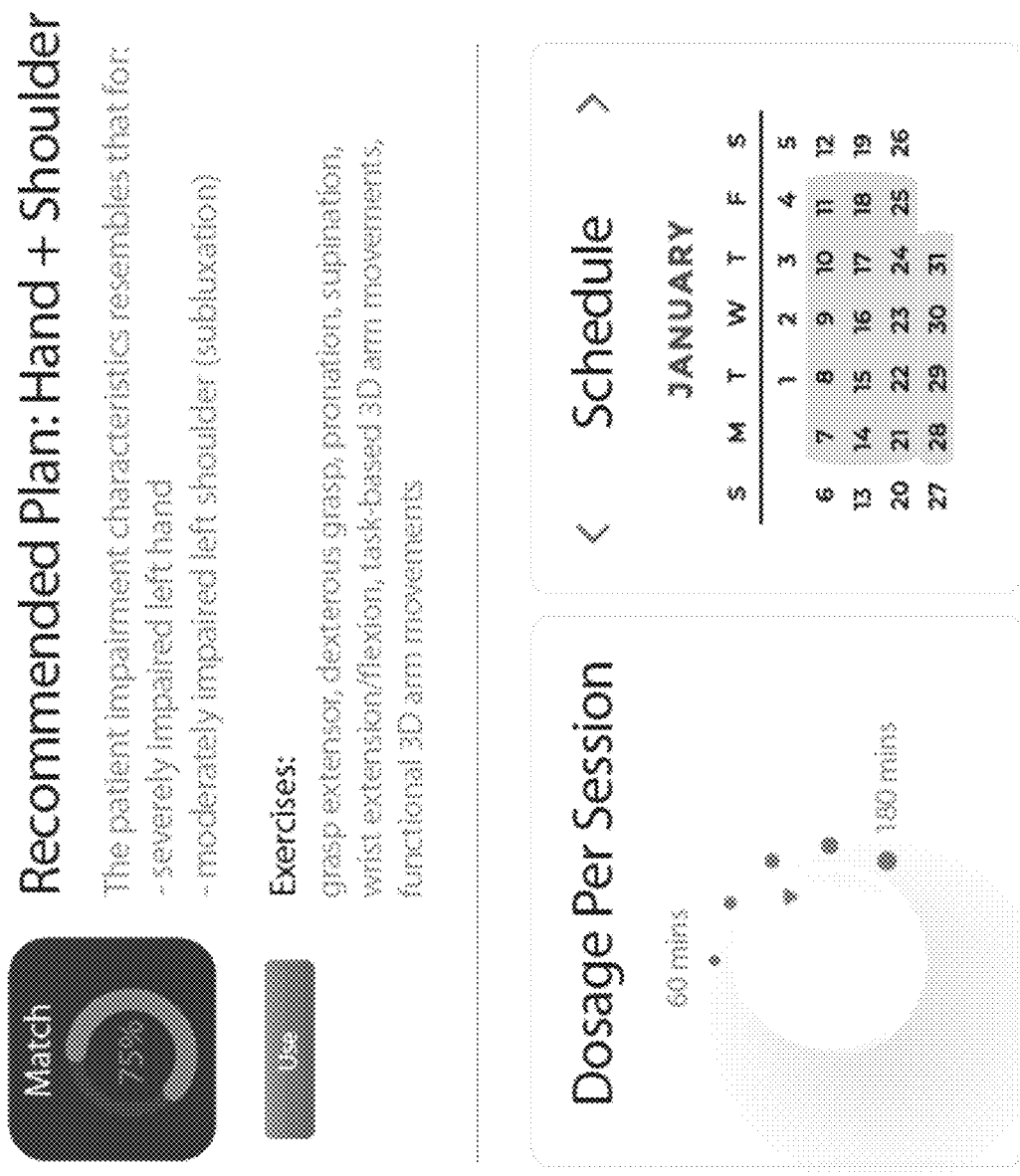
FIGS. 22 and 23 illustrate user interfaces for adjusting assessment and therapy parameters in an exemplary system of assessment and therapy in accordance with embodiments.
Figure 23:
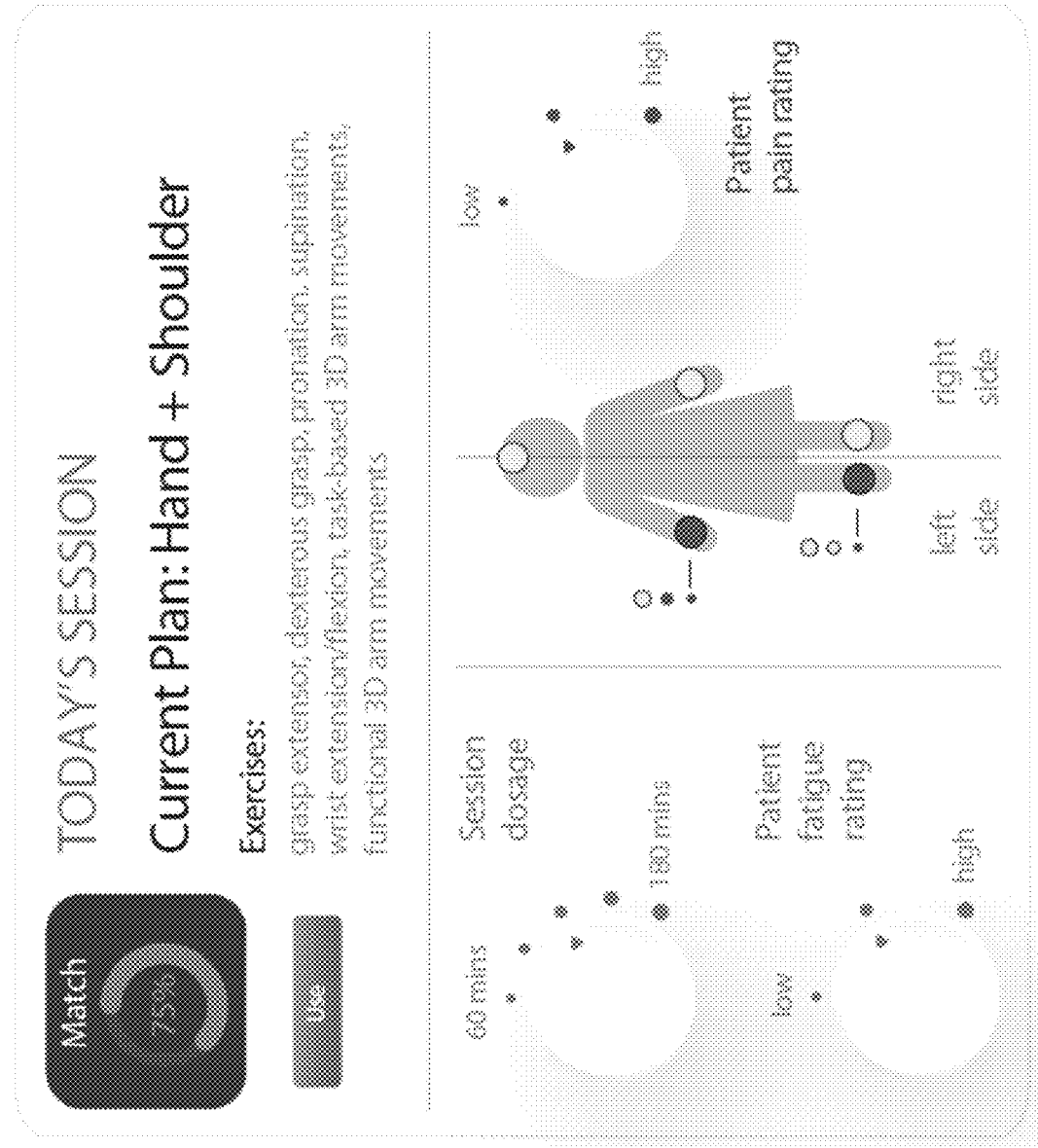

After a therapist enters (or automatically assesses a patient's impairment prole), all the work done to estimate a therapy plan (appropriate activities+schedule+dosage) is done behind-the-scenes. At this point, the therapist is shown the top three digital therapy recommendations that best explain the patient's impairment prole. The therapist is fully in control of selecting whether they want to go with one of the recommended plans, or customize any of the plans, or completely build a therapy plan from scratch by themselves. The interface is designed to provide only the key parameters that the therapist requires to understand and chose a plan (appropriate activities/exercises, schedule & dosage). Prior to starting each session associated with a plan, the therapist is able to modulate the session time (within reason) and enter the patient's current fatigue and body-part pain ratings. FIGS. 22 and 23 illustrate exemplary user interfaces for adjusting such parameters.

At step 1406, the therapy plan is tuned. Despite best efforts, the therapy plan might not be fully matched to a patient's impairment level. If individual activities within the therapy plan are too easy or too difficult, then the patient will become demotivated, leading to reduced time-on-task. Thus, at this step, embodiments can provide parameters to a therapist or other user to modulate the difficulty of individual activities within a therapy plan to the nature and severity of the patient's impairment profile.

The production of any complex sensorimotor task relies on the action-perception loop. Patients will perceive information, process it to produce motor output in order to interact with the world. In the case of digital-based activities as those provided by embodiments as described herein, the difficulty of the activity or game is further influence by the nature of the patient's impairment (e.g., motor vs. cognitive). Thus, preferred embodiments include parameters controls based on the nature and severity of the patient's impairment.

Figure 24:
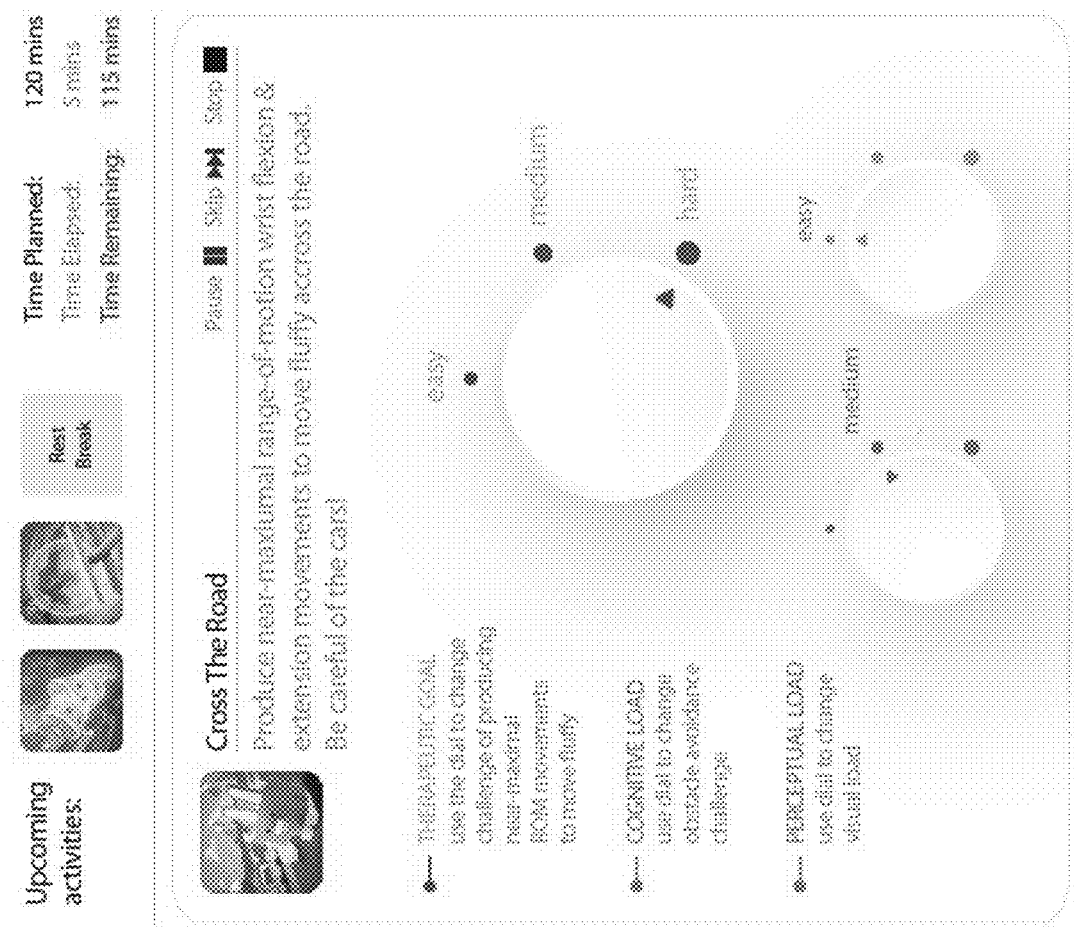
FIG. 24 illustrates a user interface for difficulty parameters in an exemplary system of assessment and therapy in accordance with embodiments.

To enable this modulation, preferred embodiments display one or more parameter options in a user interface for a user to set a value. The values are then used to adjust aspects of the activity. Each activity has a specific set of one or more parameters that influence the difficulty. Despite all games being influence by the interaction between the action-perception loop and the patient's impairment profile, since the game logic of each activity is different, the parameters that influence each game's difficulty are different. In the most extreme case, the parameters for two games might be completely different. Thus, what is required is the flexibility of designing activities with different game logics, while providing a unified experience for therapists in order to control the difficulty of a wide portfolio of disparate activities. In preferred embodiments, the user interface includes 3 elements that are consistent across all activities and that correspond to the elements of the action-perception loop (perceptual load, cognitive load, motor output). Each activity parameter maps in an individualized way onto the user interface elements. In some embodiments, the user interface elements for the difficulty parameters can have limited number of settings for ease of use. An exemplary illustration of a user interface in accordance with the difficulty parameters in such an embodiment is shown in FIG. 24.

At step 1408, the patient's nature and impairment severity are assessed. Judging the efficacy of a therapy plan requires that a patient's impairment profile is measured at frequent intervals and compared to pre-intervention baseline. In some preferred embodiments, assessment metrics can be received by the system during activities for therapy of purpose-built games that capture the relevant impairment metrics during the appropriate movements required within the activity. The table below provides an example of the corresponding impairment, assessment activity, and source of the impairment metrics that can be received during activities.

| Impairment | Assessment Activity | Peripheral |
|---|---|---|
| Hand Open/ Close | Gamified grasp flexion/ extension task | Hand device for quantifying grasp force |
| Finger Independence | Gamified finger individuation task | Finger individuation device |
| Flexor Synergy | Gamified 3D reach to grasp task | Multi-muscle recording from upper-limb extensors + flexors |
| Extensor Synergy | Gamified 3D reach to grasp task | Multi-muscle recording from upper-limb extensors + flexors |
| Shoulder Flexion | Gamified 3D reach to grasp task | Markerless tracking + Hand device to encourage reach to grasp behavior |
| Elbow Extension | Gamified elbow extension task | Markerless tracking |
| Pronation/ Supination | Gamified 3D pointing task | Markerless tracking + Hand device to encourage pronation/supination behavior |

Figure 25:
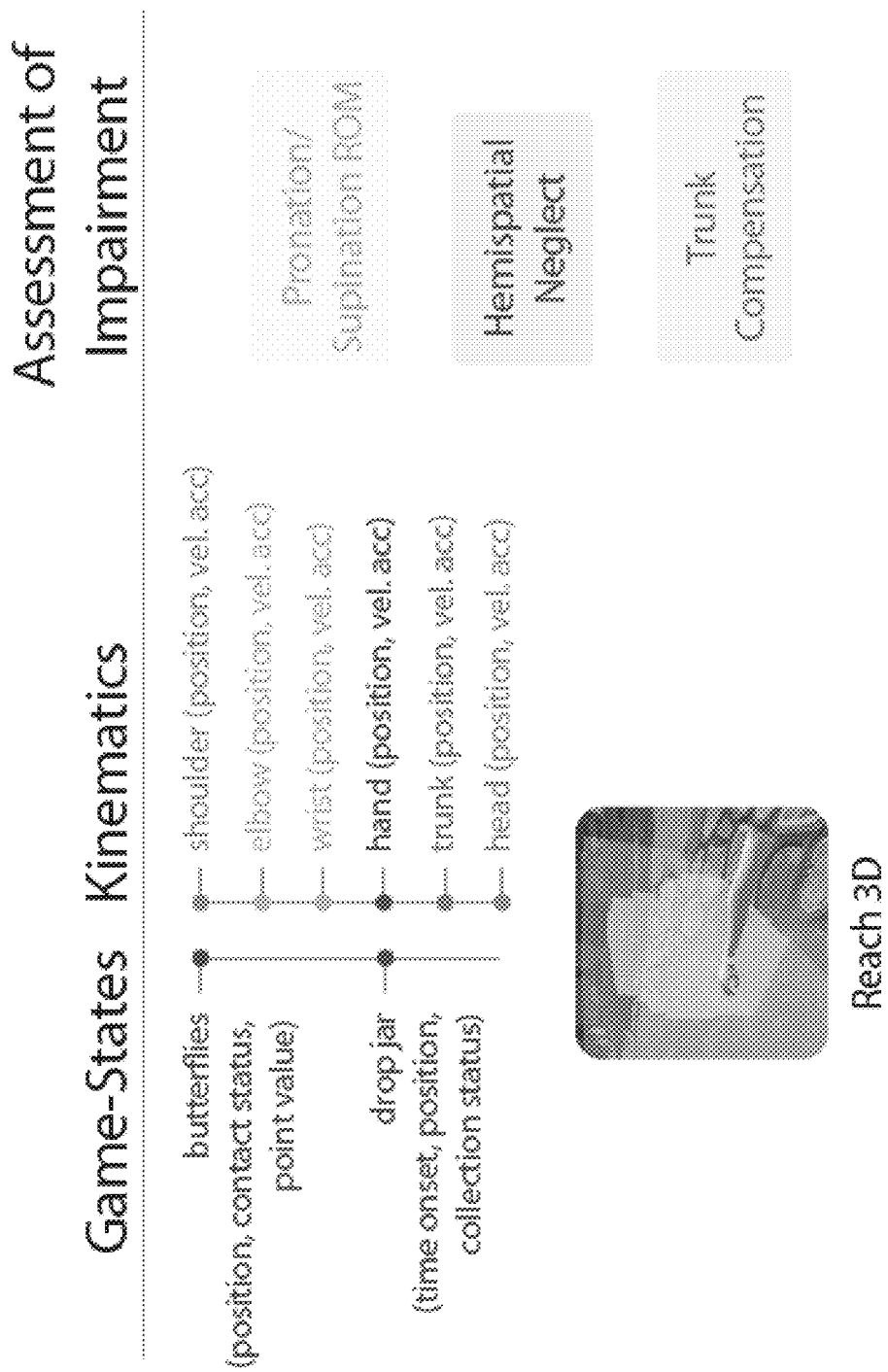
FIG. 25 illustrates a user interface showing the relationship between game-states and corresponding kinematics in an exemplary system of assessment and therapy in accordance with embodiments.

In preferred embodiments, each activity generates a combination of kinematic metrics for all of the body areas used during the activity and game-states data. In some cases, full-body kinematic metrics are generated during an activity, even for areas that are not targeted during the activity. In this way, assessment can be done on secondary effects such as compensation. For some purpose-built activities, this data contains information regarding the impairment features of interest, allowing the system to capture and populate snapshots of a patient's impairment over time during gameplay. FIG. 25 illustrates an exemplary user interface of showing the relationship between game-states, corresponding kinematics for which data is generated and corresponding impairments assessed.

Figure 26:
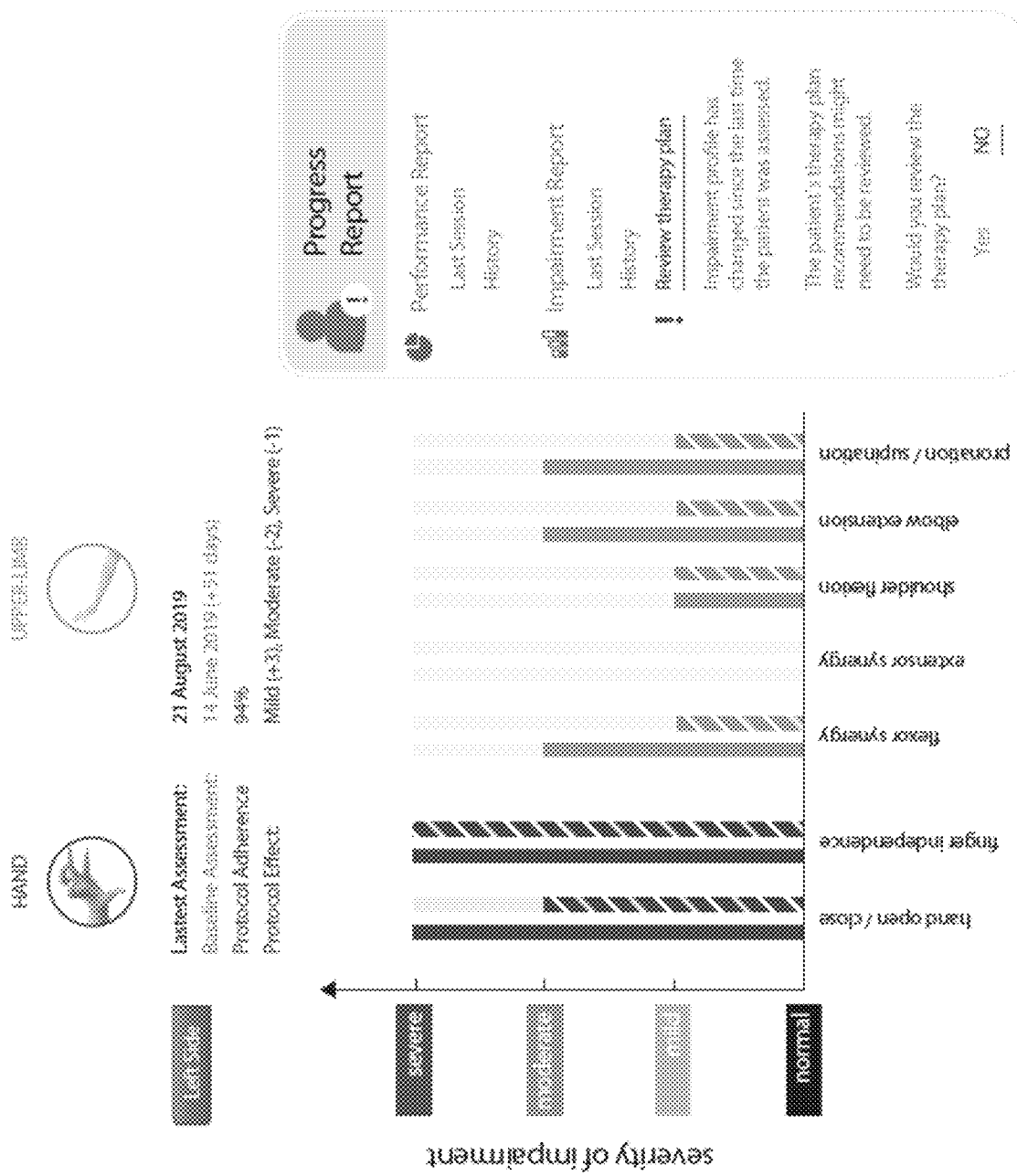
FIG. 26 illustrates a user interface showing therapy progress in an exemplary system of assessment and therapy in accordance with embodiments.

At step 1410, therapy plan efficacy metrics are determined. Preferred embodiments include a repository that provides a snapshot of a patient's performance and impairment during the course of therapy. Since the patient's impairment profile is periodically measured during therapy on a frequent bases through assessments during gamified assessment sessions and therapy activities themselves, the difference between the initial baseline assessment and the current assessment profile can be quantified. For example, in accordance with the exemplary illustration of a user interface in FIG. 26, there has been some improvement in the patient's impairment, specifically impairment in the arm has improved from moderate to mild. Thus, the therapist is prompted to review the therapy plan in order to determine whether the plan needs to be updated in order to account for the impairment change.

Figure 27:
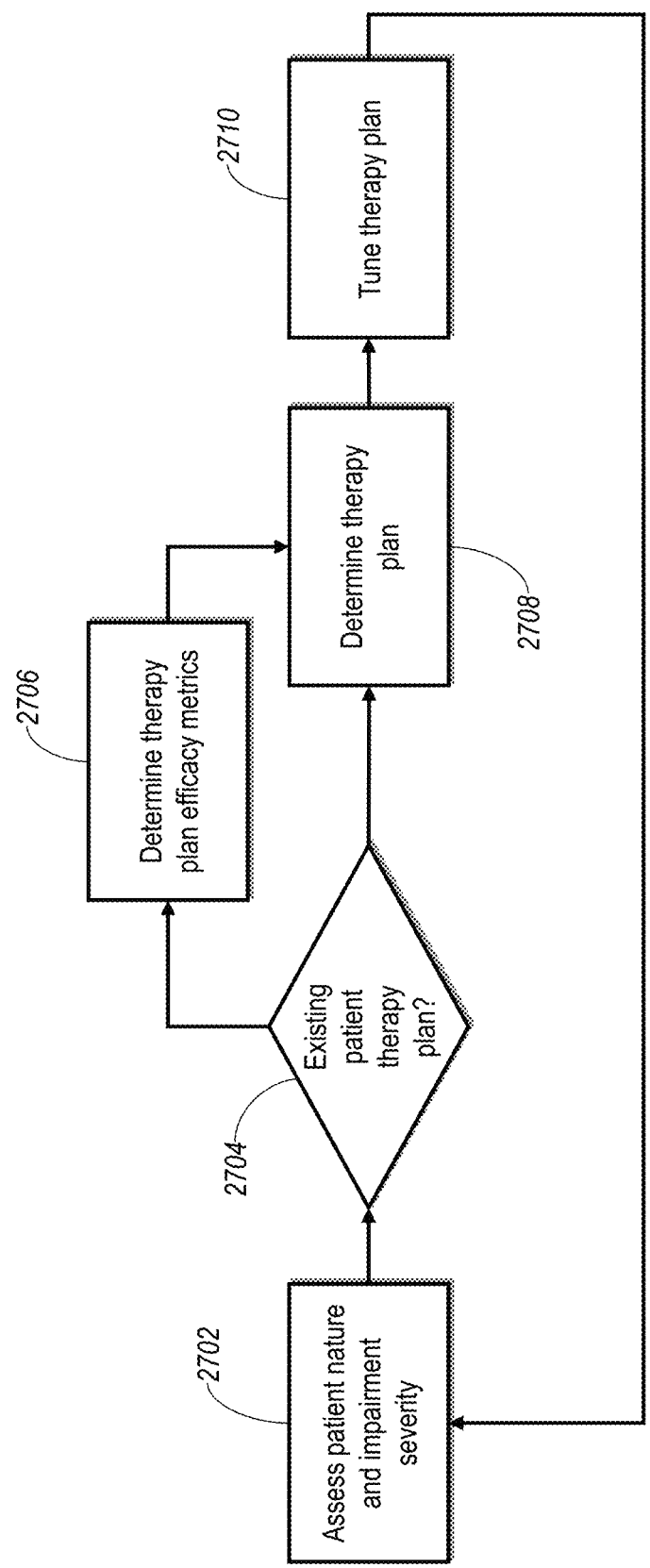
FIG. 27 illustrates a flowchart of an exemplary method for closed-loop assessment and treatment of a neurological condition in accordance with embodiments.

FIG. 27 illustrates an exemplary flowchart of a method 2700 for closed-loop assessment and treatment of a neurological condition. At step 2702, the nature and severity of impairment is assessed. At step 2704, it is determined whether there is an existing therapy plan. If there is, then at step 2706, therapy plan efficacy metrics are determined. At step 2708, a therapy plan is determined. At step 2710, the therapy plan is tuned.

Any and all references to publications or other documents, including but not limited to, patents, patent applications, articles, webpages, books, etc., presented in the present application, are herein incorporated by reference in their entirety.

Example embodiments of the devices, systems and methods have been described herein. As noted elsewhere, these embodiments have been described for illustrative purposes only and are not limiting. Other embodiments are possible and are covered by the disclosure, which will be apparent from the teachings contained herein. Thus, the breadth and scope of the disclosure should not be limited by any of the above-described embodiments but should be defined only in accordance with claims supported by the present disclosure and their equivalents. Moreover, embodiments of the subject disclosure may include methods, systems and apparatuses which may further include any and all elements from any other disclosed methods, systems, and apparatuses, including any and all elements corresponding to target particle separation, focusing/concentration. In other words, elements from one or another disclosed embodiment may be interchangeable with elements from other disclosed embodiments. In addition, one or more features/elements of disclosed embodiments may be removed and still result in patentable subject matter (and thus, resulting in yet more embodiments of the subject disclosure). Correspondingly, some embodiments of the present disclosure may be patentably distinct from one and/or another reference by specifically lacking one or more elements/features. In other words, claims to certain embodiments may contain negative limitation to specifically exclude one or more elements/features resulting in embodiments which are patentably distinct from the prior art which include such features/elements.

What is claimed is:

1. A device for providing dexterous hand function assessment and therapy, comprising:
    a first portion of flexible material forming a cavity;
    a second portion of non-flexible material;
    a pressure sensor;
    a wireless transceiver;
    a power storage unit;
    a sensor device;
    a printed circuit board (PCB) coupled to the second portion; and
    wherein a portion of an edge of the first portion is configured to create a semi-hermetic seal with at least a portion of an edge of the second portion, and the PCB has connected thereto the pressure sensor, the wireless transceiver, and the power storage unit;
    wherein said pressure sensor comprises a barometer for measuring pressure within said cavity;
    wherein a temperature reading from said sensor device is provided from within said cavity to form temperature data;
    wherein said temperature data and said pressure data are transmitted from the device through said wireless transceiver, for determination of an external force applied to said first portion of flexible material.

2. The device of claim 1, further comprising a valve through the second portion and wherein the second portion includes a flat facet.

3. The device of claim 2, further comprising one or more inertial measurement units (IMU) and a memory storage device.

4. The device of claim 3, wherein the first portion comprises a graphical component to enable position and orientation tracking of the device.

5. The device of claim 3, further comprising an active marker to enable position and orientation tracking of the device.

6. The device of claim 5, further comprising a third portion through which the active marker is visible.

7. A method for the assessment and therapy of dexterous hand function, comprising:
    establishing a connection with the hand device of claim 1;
    establishing a hand selection assigned to the hand device;
    receiving a first barometric pressure of the interior of the hand device;
    sending an instruction to an idle pressure controller indicating the barometric pressure is a baseline.

8. The device of claim 7, further comprising a valve through the second portion; wherein said valve allows air pressure on an interior of the device to adjust to equilibrium with ambient air pressure.

9. The device of claim 8, further comprising a reset button to place pressure on said valve to adjust said air pressure.

10. The device of claim 8, wherein the second portion includes a flat facet, located at a bottom of the device; wherein said non-flexible material of said second portion does not deform under the weight of the device when the device is resting on said flat surface.

11. The device of claim 1, wherein said temperature data and said pressure data are transmitted for calibrating the device for being manually manipulated.

12. The device of claim 11, wherein a force exerted upon said first portion of flexible material upon manual manipulation is determined according to said temperature data and said pressure data.

13. The device of claim 1, wherein said second portion comprises a stationary and non-deformable anchor point, and wherein said PCB is anchored to said anchor point.

14. The device of claim 7, wherein said wireless transmission comprises at least one of Bluetooth, cellular data, or RFID.

15. A system for providing dexterous hand function assessment and therapy, comprising:
    a device for providing dexterous hand function assessment and therapy, comprising:
        a first portion of flexible material forming a cavity;
        a second portion of non-flexible material; a printed circuit board (PCB) coupled to the second portion;
        a pressure sensor;
        a wireless transceiver;
        a power storage unit;
        a sensor device; and
        wherein a portion of an edge of the first portion is configured to create a semi-hermetic seal with at least a portion of an edge of the second portion, and the PCB has connected thereto the pressure sensor, the wireless transceiver, and the power storage unit;
        wherein said pressure sensor comprises a barometer for measuring pressure within said cavity;
    a base station comprising a battery charging component, the battery charging component including a cooling system; and
    the system further comprising an external computational device;
    wherein a temperature reading from said sensor device is provided from within said cavity to form temperature data:
    wherein the pressure within the device is determined according to said barometer sensor data from said pressure sensor and said temperature data; and wherein an applied force to the device is determined by said external computational device according to the pressure and the temperature data.

16. The system of claim 15, wherein calibration data is received by said external computational device, said calibration data comprising a first barometric pressure of the interior of the device; wherein said first barometric pressure is a baseline.

17. The system of claim 16, wherein a calibration process is performed with a user manipulating the device, wherein said calibration process further comprises performing a plurality of manipulations of the device, comprising a movement of the device and a grip on the device, to determine at least one of user range of motion, a maximum pressure for gestures, a minimum acceleration, a maximum acceleration, or a combination thereof.

18. The system of claim 17, wherein said user range of motion is determined from accelerometer data.

19. The system of claim 18, wherein said user range of motion comprises wrist flexion/extension, and wherein a range of motion of wrist flexion/extension is determined by deriving a first plane from an acceleration vector when the device is held by the user at maximum wrist flexion, and by deriving a second plane when the device is held by the user at maximum wrist extension; wherein said range of motion is determined according to an angle between these two vectors on the plane.

20. The system of claim 19, wherein said wireless transmission comprises at least one of Bluetooth, cellular data, or RFID.

21. The system of claim 20 wherein the device comprises a processor for operating firmware, wherein said firmware controls a connection between the device and said external computational device, for streaming data from the device to said external computational device.

22. The system of claim 21, wherein said streaming data is streamed as packets, according to one or more streaming data parameters to select and configure packet content, comprising one or more of timestamp data, acceleration data, gyroscope data, barometer data, temperature data, pressure/force normalization data, or quaternion data, or a combination thereof.

23. The system of claim 22, wherein said accelerometer data is processed through a signal processing to dampen a signal from said accelerometer with minimal impact on latency for use during calibration and activity use.

* * * * *